United States Patent
Li

(10) Patent No.: US 10,864,257 B2
(45) Date of Patent: *Dec. 15, 2020

(54) METHOD FOR PREVENTION OR TREATMENT OF ACUTE AND CHRONIC THROMBOSIS

(71) Applicant: TALENGEN INTERNATIONAL LIMITED, Hong Kong (CN)

(72) Inventor: Jinan Li, Guangdong (CN)

(73) Assignee: TALENGEN INTERNATIONAL LIMITED, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/063,534

(22) PCT Filed: Dec. 16, 2016

(86) PCT No.: PCT/CN2016/110448
§ 371 (c)(1),
(2) Date: Jun. 18, 2018

(87) PCT Pub. No.: WO2017/101866
PCT Pub. Date: Jun. 22, 2017

(65) Prior Publication Data
US 2019/0247472 A1    Aug. 15, 2019

(30) Foreign Application Priority Data

Dec. 18, 2015  (WO) ................ PCT/CN2015/097941

(51) Int. Cl.
| A61K 38/00 | (2006.01) |
| A61K 38/48 | (2006.01) |
| A61P 27/02 | (2006.01) |
| A61P 7/02 | (2006.01) |
| A61P 25/02 | (2006.01) |
| A61P 9/14 | (2006.01) |

(52) U.S. Cl.
CPC ................ *A61K 38/48* (2013.01); *A61P 7/02* (2018.01); *A61P 9/14* (2018.01); *A61P 25/02* (2018.01); *A61P 27/02* (2018.01); *C12Y 304/21007* (2013.01)

(58) Field of Classification Search
None
See application file for complete search history.

(56) References Cited

U.S. PATENT DOCUMENTS

| 5,637,299 | A | 6/1997 | McDonagh et al. |
| 2003/0026798 | A1 | 2/2003 | Zimmerman et al. |
| 2012/0114630 | A1 | 5/2012 | Zwaal |
| 2018/0369345 | A1 | 12/2018 | Li |
| 2019/0015485 | A1 | 1/2019 | Li |

FOREIGN PATENT DOCUMENTS

| CA | 1768138 | | 5/2006 | |
| CN | 1451746 | A * | 10/2003 | |
| CN | 101015686 | | 8/2007 | |
| CN | 102199587 | | 9/2011 | |
| CN | 102482338 | | 5/2012 | |
| EP | 0674906 | | 10/1995 | |
| JP | 62-153224 | | 7/1987 | |
| JP | 2019-500423 | | 1/2019 | |
| JP | 2019-500424 | | 1/2019 | |
| WO | WO9512407 | | 5/1995 | |
| WO | WO 2011/004011 | | 1/2011 | |
| WO | WO-2011004011 | A1 * | 1/2011 | ........... A61K 38/484 |
| WO | WO2017077380 | | 5/2011 | |

OTHER PUBLICATIONS

Yuan guiqing, Thrombotic disease has become an important disease that threatens human health and life. Chinese Journal of Laboratory Medicine, 2004,8(27)487.
Alexander CM and Werb, Z. (1991). Extracellular matrix degradation. In Cell Biology of Extracellular Matrix, Hay ED, ed. (New York: Plenum Press), pp. 255-302.
Werb, Z., Mainardi, C.L., Vater, C.A., and Harris, E.D., Jr. (1977). Endogenous activiation of latent collagenase by rheumatoid synovial cells. Evidence for a role of plasminogen activator. N. Engl. J. Med. 296, 1017-1023.
He, C.S., Wilhelm, S.M., Pentland, A.P., Marmer, B.L., Grant, G.A., Eisen, A.Z., and Goldberg, G.I. (1989). Tissue cooperation in a proteolytic cascade activating human interstitial collagenase. Proc. Natl. Acad. Sci. U. S. A 86, 2632-2636.
Stoppelli, M.P., Corti, A., Soffientini, A., Cassani, G., Blasi, F., and Assoian, R.K. (1985). Differentiation-enhanced binding of the aminoterminal fragment of human urokinase plasminogen activator to a specific receptor on U937 monocytes. Proc. Natl. Acad. Sci. U. S. A 82, 4939-4943.
Vassalli, J.D., Baccino, D., and Belin, D. (1985). A cellular binding site for the Mr 55,000 form of the human plasminogen activetor, urokinase. J. Cell Biol. 100, 86-92.
Wiman, B. and Wallen, P. (1975). Structural relationship between "glutamic acid" and "lysine" forms of human plasminogen and their interaction with the NH2-terminal activation peptide as studied by affinity chromatography. Eur. J. Biochem. 50, 489-494.
Saksela, O. and Rifkin, D.B. (1988). Cell-associated plasminogen activation: regulation and physiological functions. Annu. Rev. Cell Biol. 4, 93-126.
Raum, D., Marcus, D., Alper, C.A., Levey, R., Taylor, P.D., and Starzl, T.E. (1980). Synthesis of human plasminogen by the liver. Science 208, 1036-1037.

(Continued)

*Primary Examiner* — Jeanette M Lieb
(74) *Attorney, Agent, or Firm* — Hauptman Ham, LLP

(57) ABSTRACT

The present invention relates to the use of plasminogen in the dissolution of fresh and old thrombus. Compared with other existing thrombolytic drugs, the plasminogen of the present invention can specifically dissolve thrombus without causing side effects such as bleeding. The drug of the present invention also has the advantages of dissolving both fresh and old thrombus, with a long half-life and controllable thrombolytic strength. Therefore, plasminogen may become a brand-new strategy for dissolving thrombus in vivo.

11 Claims, 8 Drawing Sheets

Specification includes a Sequence Listing.

(56) References Cited

OTHER PUBLICATIONS

Wallén P (1980). Biochemistry of plasminogen. In Fibrinolysis, Kline DL and Reddy KKN, eds.
Sottrup-Jensen, L., Zajdel, M., Claeys, H., Petersen, T.E., and Magnusson, S. (1975). Amino-acid sequence of activation cleavage site in plasminogen: homology with "pro" part of prothrombin. Proc. Natl. Acad. Sci. U. S. A 72, 2577-2581.
Collen, D. and Lijnen, H.R. (1991). Basic and clinical aspects of fibrinolysis and thrombolysis. Blood 78, 3114-3124.
Alexander, C.M. and Werb, Z. (1989). Proteinases and extracellular matrix remodeling. Curr. Opin. Cell Biol. 1, 974-982. [14]Mignatti, P. and Rifkin, D.B. (1993). Biology and biochemistry of proteinases in tumor invasion. Physiol Rev. 73, 161-195.
Collen, D. (2001). Ham-Wasserman lecture: role of the plasminogen system in fibrin-homeostasis and tissue remodeling. Hematology. (Am. Soc. Hematol. Educ. Program. ) 1-9.
Rifkin, D.B., Moscatelli, D., Bizik, J., Quarto, N., Blei, F., Dennis, P., Flaumenhaft, R., and Mignatti, P. (1990). Growth factor control of extracellular proteolysis. Cell Differ. Dev. 32, 313-318.
Andreasen, P.A., Kjoller, L., Christensen, L., and Duffy, M.J. (1997). The urokinase-type plasminogen activator system in cancer metastasis: a review Int. J. Cancer 72, 1-22.
Rifkin, D.B., Mazzieri R., Munger, J.S., Noguera, I., and Sung, J. (1999). Proteolytic control of growth factor availability. APMIS 107, 80-85.
Hillis LD, et.al. . High dose intravenous streptokinase for acute myocardial infarction: preliminary results of a multicenter trial. J Am Coll Cardiol.1985; 6:957-962.
Smalling RW. A fresh look at the molecular pharmacology of plasminogen activators: from theory to test tube to clinical outcomes. Am J Health-Syst Pharm 1997; 54(suppl 1):S17-S22.
Nobel S, McTavish D. Reteplase: a review of it pharmacological properties and clinical efficiency in the management of acute myocardial infarction. [J]. Drug, 1996, 52(4):589-605.
Abdoli-Nasab M1, Jalali-Javaran M, Expression of the truncated tissue plasminogen activator (K2S) gene in tobacco chloroplast, Mol Biol Rep (2013) 40:5749-5758.
Gottlob R. (1975) Plasminogen and plasma inhibitors inarterial and venous thrombi of various ages. In: Progress inchemical fibrinolysis and thrombolysis. vol. 1. Raven Press,New York, pp. 23-36.
Sabovic M, Lijnen HR, Keber D, Collen D. (1989) Effect ofretraction on the lysis of human clots with fibrin specific andnon-fibrin specific plasminogen activators. Thromb Haemost,62, 1083-1087.
Potter van Loon BJ, Rijken DC, Brommer EJ, van der MaasAP. (1992) The amount of plasminogen, tissue-type plasminogen activator and plasminogen activator inhibitor type 1 in human thrombi and the relation to ex-vivo lysibility. Thromb Haemost, 67, 101-105.
Hacke W, Kaste M, Bluhmki E, Brozman M, Dávalos A et al. (2008)Thrombolysis with alteplase 3 to 4.5 hours after acute ischemic stroke.N Engl J Med 359: 1317-1329.
Lees KR, Bluhmki E, von Kummer R, Broil TG, Toni D et al. (2010)Time to treatment with intravenous alteplase and outcome in stroke: anupdated pooled analysis of Ecass, Atlantis, Ninds, and Epithet trials. Lancet 375.
Marder V J, Novokhatny V. Direct fibrinolytic agents: biochemical attributes, preclinical foundation and clinical potential [J]. Journal of Thrombosis and Haemostasis, 2010, 8(3): 433-444.
Hunt J A, Petteway Jr S R, Scuderi P, et al. Simplified recombinant plasmin: production and fu-nctional comparison of a novel thrombolytic molecule with plasma-derived plasmin [J]. Thromb Haemost, 2008, 100(3): 413-419.
Sottrup-Jensen L, Claeys H, Zajdel M, et al. The primary structure of human plasminogen: Isolation of two lysine-binding fragments and one "mini"-plasminogen (MW, 38,000) by elastase-catalyzed-specific limited proteolysis [J]. Progress in chemical fibrinolysis and thrombolysis, 1978, 3: 191-209.
Nagai N, Demarsin E, Van Hoef B, et al. Recombinant human microplasmin: production and potential therapeutic properties [J]. Journal of Thrombosis and Haemostasis, 2003, 1(2): 307-313.

Valery V. Novokhatny,Gary J. Jesmok,Locally delivered plasmin: why should it be superior to plasminogen activators for direct thrombolysis ,Trends in Pharmacological Sciences vol. 25 No. 2 Feb. 2004.
V. Novokhatny, K. Talylor and T. P. Zimmerman,Thrombolytic potency of acid-stabilized plasmin: superiority over tissue-type plasminogen activator in an in vitro model of catheter-assisted thrombolysis,Journal of Thrombosis and Haemostasis, 1: 1034-1041.
F Bachmann,Springer,Fibrinolytics and antifibrinolytics,2001, 146(4):670.
R. B. Aisina1 and L. I. Mukhametova, Structure and Function of Plasminogen/Plasmin System, Russian Journal of Bioorganic Chemistry, 2014, vol. 40, No. 6, pp. 590-605.
Kyle Landskroner, MS, Neil Olson, DVM, PhD, and Gary Jesmok, PhD,Cross-Species Pharmacologic Evaluation of Plasmin as a Direct-Acting Thrombolytic Agent:Ex Vivo Evaluation for Large Animal Model Development, J Vasc Interv Radiol 2005; 16:369-377.
Edvin L.Madison,Gary S.Coombs,and Dacid R.Corey,Substrate Specificity of Tissue Type Plasminogen Activator ,The Journal of biological,Chemistry, 1995, vol. 270, No. 13, pp. 7558-7562.
Kei Takahashi, Hau C. Kwaan, Enki Koh, ardMasatakaTanabe,Enzymatic Properties of the Phosphorylated Urokinase-Type Plasminogen Activator Isolated From A Human Carcinomatous Cell Line,Biochemical and Biophysical Research Communications , 1992 pp. 1473-1481.
Hui YH, Huang NH, Ebbed L et al. Pharmacokinetic comparisons of tail-bleeding with cannula- or retro-orbital bleeding techniques in rats using six marketed drugs. J Pharmacol Toxicol Methods. Sep.-Oct. 2007;56(2):256-64.
Jae Kyu Ryu, Mark A. Petersen, Sara G. Murray et al. Blood coagulation protein fibrinogen promotes autoimmunity and demyelination via chemokine release and antigen presentation. Nature Communications,2015,6:8164.
Dimitrios Davalos , Katerina Akassoglou. Fibrinogen as a key regulator of inflammation in disease. Seminars in Immunopathology,2012. 34(1):43-62.
Valvi D, Mannino DM, Mullerova H, et al. Fibrinogen, chronic obstructive pulmonary disease (COPD) and outcomes in two United States cohorts. Int J Chron Obstruct Pulmon Dis 2012;7:173-82.
International Search Report dated Mar. 23, 2017 from corresponding application No. PCT/CN2016/110448.
TW Office Action with English translation from corresponding application No. TW 105141905.
N Kaur, PK Sinha, G Sahni. Site-specific PEGylation of microplasmin for improved thrombolytic therapy through engineering enhanced resistance against serpin mediated inhibition. PLoS ONE 14(5): e0217234.
Aisina R B, Mukhametova Li. Structure and function of plasminogen/plasmin system [J]. Russian Journal of Bioorganic Chemistry, 2014, 40(6):590-605.
Kim JS. tPA Helpers in the Treatment of Acute Ischemic Stroke: Are They Ready for Clinical Use? J Stroke. May 2019; 21(2):160-174.
Badylak S F, Voytik S L, Henkin J, et al. The Beneficial Effect of Lys-Plasminogen upon the Thrombolytic Efficacy of Urokinase in a Dog Model of Peripheral Arterial Thrombosis [J]. Pathophysiology of Haemostasis and Thrombosis, 1991, 21(5):278-285.
Plow, E.F. et al., "The Functions of Plasminogen in Cardiovascular Disease", Trends Cardiovasc Med., vol. 14, No. 5, Jul. 31, 2004 (Jul. 31, 2004), pp. 180-186.
Stephen F.Badylak, Enhancement of the Thrombolytic Efficacy of Prourokinase by Lys-Plasminogen in a Dog Model of Artbrial Thrombosis,.Thrombosis Research, 1991, vol. 62, p. 115-126.
Sarah X. Zhang et al: "Therapeutic Potential of Angiostatin in Diabetic Nephropathy", Journal of the Amer1can Society OfNephrology, vol. 17 , No. 2,Jan. 1, 2006 (Jan. 1, 2006), pp. 475-486.
K.Anderle et al.,Review of Studies with Plasminogen Concentrates and Proposals for Further Therapeutic Strategies with Plasminogen Concentrates,Heamostasis, 1988, vol. 18, Suppl.1, p. 165-175.
Joseph J et al.,Plasminogen-enriched Pulse-Spray Thrombolysis with tPA:Further Development,Thrombosis Research, 1991, vol. 62, p. 115-126.

(56) References Cited

OTHER PUBLICATIONS

Sima J et al: "The effect of angiostatin on vascular leakage and VEGF expression in rat retina", FEBS Lett , Elsevier ,Amsterdam, N L,vol. 564 , No. 1-2 ,Apr. 23, 2004 (Apr. 23, 2004) ,pp. 19-23.
Office Action dated Jul. 3, 2019 from corresponding application No. CN 201611194744.
The extended European search report dated May 15, 2019 from corresponding application No. EP 16874923.2.
Office Action dated May 21, 2019 from corresponding application No. JP 2018-550633.
1. Rijken D C, Sakharov D V. Basic Principles in Thrombolysis: Regulatory Role of Plasminogen [J]. Thrombosis Research, 2001, 103 Suppl 1:S41-9.
2. FrancËois Nantel, Danielle Denis, Robert Gordon et al.Distribution and regulation of cyclooxygenase-2 in carrageenan-induced inflammation. Br J Pharmacol. Oct. 1999;128(4):853-9.
3. V. Novokhatny, K. Taylor and T. P. Zimmerman, Thrombolytic potency of acid-stabilized plasmin: superiority over tissue-type plasminogen activator in an in vitro model of catheter-assisted thrombolysis, Journal of Thrombosis and Haemostasis, 2003; 1: 1034-1041.

\* cited by examiner

METHOD FOR PREVENTION OR TREATMENT OF ACUTE AND CHRONIC THROMBOSIS

RELATED APPLICATIONS

The present application is a National Phase of International Application Number PCT/CN2016/110448, filed Dec. 16, 2016, and claims the priority of International Application No. PCT/CN2015/097941, filed Dec. 18, 2015.

FIELD OF THE INVENTION

The invention relates to a new method for preventing and/or treating thrombosis by using plasminogen. Plasminogen can specifically dissolve thrombus without causing side effects such as bleeding. The drug of the present invention also has the advantages of being able to dissolve fresh and old thrombus and having a long half-life period and controllable thrombolytic strength. Therefore, plasminogen may become a brand-new strategy for dissolving thrombus in vivo.

BACKGROUND OF THE INVENTION

The formation and harm of thrombus Thrombus refers to blood clots that are abnormally formed from elements in circulating blood, or blood deposits that occur on inner heart wall or blood vessel wall. It comprises myocardial infarction, cerebral embolism, pulmonary thrombosis/thromboembolism, deep vein thrombosis, peripheral vascular embolism, etc. It is a disease that seriously harms human health. Its morbidity, disability and mortality rates are high. According to the statistics of the World Health Organization, the number of people who die from thromboembolism in the world is about 26 million each year, which is far larger than that from other causes of death, becoming the number one enemy to human health[1].

Plasmin is a key component of the plasminogen activation system (PA system). It is a broad-spectrum protease that can hydrolyze several components of the extracellular matrix (ECM), including fibrin, gelatin, fibronectin, laminin and proteoglycans[2]. In addition, plasmin can activate some pro-metalloproteinases (pro-MMP) to form active metalloproteinases (MMP). Therefore, plasmin is considered to be an important upstream regulator of extracellular proteolysis[3, 4]. Plasmin is formed by proteolysis of plasminogen by two physiological PAs: tissue plasminogen activator (tPA) or urokinase plasminogen activator (uPA). Due to the relatively high level of plasminogen in plasma and other body fluids, it is traditionally believed that the regulation of PA system is mainly achieved through the synthesis and activity level of PA. The synthesis of PA system components is strictly regulated by different factors such as hormones, growth factors and cytokines. In addition, there also exist specific physiological inhibitors of plasmin and PA. The main inhibitor of plasmin is α2-antiplasmin. There are uPA-specific cell surface receptors (uPAR) that have direct hydrolytic activity on certain cell surfaces[5,6].

Plasminogen (plg) is a single-strand glycoprotein with a molecular weight of approximately 92 kDa[7, 8]. Plasminogen is mainly synthesized in the liver and is abundantly present in the extracellular fluid. The concentration of plasminogen in plasma is about 2 μM. Therefore, plasminogen is a huge potential source of proteolytic activity in tissues and body fluids[9, 10]. There are two molecular forms of plasminogen: Glutamate-plasminogen (Glu-plasminogen) and Lysine-plasminogen (Lys-plasminogen). The natural secreted and uncleaved forms of plasminogen have an amino-terminal (N-terminal) glutamic acid and are therefore referred as Glu-plasminogen. However, in the presence of plasmin, Glu-plasminogen is hydrolyzed at Lys76-Lys77 to become Lys-plasminogen. Compared to Glu-plasminogen, Lys-plasminogen has a higher affinity for fibrin and can by activated by PA at a higher rate. The Arg560-Val561 peptide bond of these two forms of plasminogen can be cleaved by uPA or tPA, leading to the formation of disulfide-linked double-strand protease plasmin[11]. The amino-terminal portion of plasminogen contains five homologous tricyclic rings, which are so-called kringles, and the carboxy-terminal portion contains a protease domain. Some kringles contain lysine binding sites that mediate the specific interaction of plasminogen with fibrin and its inhibitor α2-AP. A recently discovered 38 kDa plasminogen fragment, including kringle 1-4, is an effective inhibitor of angiogenesis. This fragment is named angiostatin and can be produced by plasminogen hydrolyzed by several proteases.

The main substrate of plasmin is fibrin, and the dissolution of fibrin is the key to prevent pathological thrombosis[12]. Plasmin also has substrate specificity for several components of ECM, including laminin, fibronectin, proteoglycans and gelatin, indicating that plasmin also plays an important role in ECM remodeling[8, 13, 14]. Indirectly, plasmin can also degrade other components of ECM by converting certain protease precursors into active proteases, including MMP-1, MMP-2, MMP-3 and MMP-9. Therefore, it has been suggested that plasmin may be an important upstream regulator of extracellular proteolysis[15]. In addition, plasmin has the ability to activate certain potential forms of growth factors[16-18]. In vitro, plasmin can also hydrolyze components of the complement system and release chemotactic complement fragments.

Existing thrombolytic therapy Current thrombolytic-related drug therapies are common non-surgical treatments including thrombolytic therapy, anticoagulant therapy, antiplatelet drugs and vasodilators. Now the most commonly used and most effective method is to use thrombolytic therapy. There are three generations of commonly used thrombolytic drugs. The first generation is represented by streptokinase (SK) and urokinase (UK). It has strong thrombolytic activity, but no thrombolytic specificity, which is prone to systemic hyperfibrinolysis and then causes bleeding[19, 20]. The second generation is represented by tissue plasminogen activator tPA, whose thrombolytic activity is better than that of SK and UK, but its half-life is short in vivo[21]. The third generation transforms the first and the second generation of drugs by using genetic engineering techniques and monoclonal techniques, but is basically in the experimental stage. These drugs are based on increasing the activator in the fibrinolytic balance, producing plasmin (Plm) to promote fibrinolysis, so as to achieve the purpose of thrombolysis[22].

Currently there are two categories of thrombolytic drugs approved. The vast majority of thrombolytic drugs use plasminogen activators, including natural and various recombinant forms of tPA, uPA and streptokinase. Plasminogen activator cannot dissolve thrombus on its own. Plasminogen molecules near the thrombus must be activated into active plasmin for thrombolysis. In recent years, active plasmin has been approved for direct local thrombolysis. The specific method is to locally release active plasmin when the catheter is passed to the thrombus site for direct thrombolysis.

Plasminogen (plg), an inactive form of plasmin (plm), is traditionally considered to be excessive and inert in the body. The thrombolytic process of the body is only realized when plasminogen is activated by its activator into active plasmin, which in turn exerts the function of dissolving fibrin clots. It is traditionally believed that plasminogen itself does not play a role in thrombolysis.

However, the present invention has surprisingly found that natural plasminogen has a good function of dissolving fresh and old thrombus, and has the advantages of good safety, easy adjustment of thrombolytic strength, good specificity, etc.

The thrombolytic mechanism of the present invention is completely different from the currently known thrombolytic strategies.

Prior art methods for thrombolysis are achieved by increasing the thrombolysis catalyst, namely plasminogen activator, including tPA, uPA, streptokinase and its derivatives, or the product of thrombolysis reaction, i.e., active plasmin. The method for dissolving thrombus of the present invention is achieved by a strategy of modulating the substrate plasminogen of the thrombolytic reaction.

Compared with thrombolytic drugs in the prior art, the plasminogen thrombolysis in the present invention has at least the following advantages.

1. Good Thrombolytic Effect

For the long thrombus and progressively constricted old thrombus formed in the case of peripheral arterial occlusion (PAO) and deep vein thrombosis (DVT), the prior art thrombolytic drugs are less effective[23-25]. And the present invention uses plasminogen or a combination of plasminogen and PA to achieve a good thrombolytic effect on the above thrombus. Therefore, the present invention can effectively solve the above problems of tPA, uPA.

2. Long Half-Life

An important feature of current thrombolytic substances is that the in vivo half-life is too short. For example, the in vivo half-life of natural uPA is 5-10 minutes, the in vivo half-life of natural tPA is 3-5 minutes, and the in vivo half-life of natural plasmin is even more transient. Even though the half-life of these substances is currently being extended through genetic engineering, the effect is unsatisfactory, and the short half-life still severely limits the application of these substances.

However, the in vivo half-life of plasminogen is as long as 53 hours, which indicates that the use of plasminogen or a combination of plasminogen and PA can significantly prolong the effect of thrombolysis in vivo, achieving the purpose of sustained and stable thrombolysis.

3. More Gentle and Controllable

For active plasmin, since it is a highly active protease, thrombolysis by using active plasmin must be a very rapid reaction process, then causing that in the current use it must be directly introduced to the thrombus through the catheter.

For plasminogen activator, since it is in the position of catalyst in the thrombolytic reaction, adding a small amount of plasminogen activator will quickly form a large amount of active plasmin in a short time, which is a dramatic enzyme reaction process.

However, the experiment of the present invention proves that the process of thrombolysis by modulating thrombolytic reaction substrate, plasminogen, is gentler.

Moreover, through the study of different amounts of plasminogen consumption and thrombolytic efficacy, the plasminogen thrombolytic rate can also be controlled by the dose of plasminogen.

4. Specificity and Low Side Effects

A major side effect of prior art using plasminogen activator as a thrombolytic drug is bleeding, especially in the intestine and brain. Since in the normal body, plasminogen is widely present in all body fluids, physiological fibrin deposition is present in the body under normal circumstances, and the increase of plasminogen activator often occurs under special conditions such as trauma, bleeding, strenuous exercise, etc. Therefore, once the plasminogen activator is injected, the reaction that plasminogen activated to form active plasmin occurs in vivo nonspecifically, then resulting in the dissolution of the original normal fibrin deposition and bleeding. Clinically, the risk of intracranial hemorrhage is a major bleeding risk. It has been reported that the incidence of intracranial hemorrhage is between 1% and 2% during the continuous administration period of 2-24 hours. There is no better way to avoid the risk of bleeding for the moment.

In the present invention, since plasminogen is not an active enzyme, the reaction of activating plasminogen to form active plasmin does not occur non-specifically after the injection of plasminogen. The site of this reaction depends on where the plasminogen activator is expressed, that is, where the thrombus occurs. The experiment of the invention proves that plasminogen can be specifically adsorbed on the thrombus site, has the specificity of thrombolysis, and the experiment proves that there is no side effect of bleeding.

5. Effectively Dissolve Old Thrombus

The thrombolytic action of current thrombolytic drugs focuses on the initial stage of thrombosis, i.e. "fresh thrombus". As demonstrated in studies in ischemic stroke, injection of recombinant tPA within 3 hours of thrombosis can effectively dissolve the thrombus. Subsequent studies have shown that recombinant tPA can dissolve the thrombus up to 4.5 hours after thrombosis. If it exceeds 4.5 hours, the risk of injection of recombinant tPA may exceed the effective effect. Therefore, in the current drug situation, it is necessary to inject recombinant tPA in the early stage of thrombosis as early as possible (less than 4.5 hours)[26, 27]. In other words, there is an urgent need in the present field to find a powerful thrombolytic drug for old thrombus.

In the present invention, the use of plasminogen alone (as well as physiological levels of tPA) or the use of plasminogen and plasminogen activator (tPA or uPA) are all effective in dissolving fresh thrombus (thrombosis for 0.5 hours), or old thrombus (20 hours), or even extremely old thrombus (72 hours). These data clearly demonstrate the great advantage of plasminogen in the dissolution of old thrombus.

Therefore, plasminogen is expected to become a new and more promising thrombolytic drug.

SUMMARY OF THE INVENTION

In one aspect, the present invention relates to a method for preventing and/or eliminating an arterial and venous thrombosis in a subject, comprising administering to the subject plasminogen. The present invention also includes the use of plasminogen for preventing and/or eliminating arterial and venous thrombosis in a subject. In one embodiment, the thrombus comprises fresh thrombus and old thrombus. In one embodiment, the thrombosis is a thrombosis caused by a blood system disease, a circulatory system disease, an autoimmune disease, a metabolic disorder disease, or an infectious disease. In one embodiment, the thrombosis is a large and/or small vascular thrombosis, and/or microvascular thrombosis, secondary to diabetes. In one embodiment, the thrombosis is a thrombosis caused by large and/or small vascular lesions.

In one aspect, the present invention relates to a novel method for preventing and/or treating thrombosis-related diseases, which comprises administering to a subject an effective amount of plasminogen. The present invention also relates to the use of plasminogen for preventing and/or treating thrombosis-related diseases. The present invention relates to a novel method for preventing and/or eliminating pathological thrombosis in a subject. The method is related to dissolving a thrombus by systemically or locally administering plasminogen. The above thrombus is a fresh thrombus and/or old thrombus. The thrombosis-related diseases are those induced or caused by a fresh thrombus and/or old thrombus. The subject is a mammal, preferably a human.

In one embodiment, the subject has a low level of plasmin or plasminogen. Specifically, the low level of plasmin or plasminogen is innate, secondary, and/or local.

In one embodiment, the thrombosis of the invention is a venous thrombosis and/or arterial thrombosis. The thrombosis-related diseases include pancreatitis and cirrhosis caused by portal vein thrombosis; renal embolism caused by renal vein thrombosis; systemic sepsis, pulmonary embolism, cerebral thrombosis caused by internal jugular vein thrombosis; organ infarctions caused by arterial thrombosis, including but not limited to: cerebral infarction, myocardial infarction, thrombotic stroke, atrial fibrillation, unstable angina pectoris, intractable angina pectoris, transient ischemic attack, pulmonary embolism, diabetes-induced large vascular embolism and/or small vascular embolism, etc.

In one embodiment, the thrombosis-related diseases are diabetic nephropathy, diabetic retinopathy, diabetic liver disease, diabetic heart disease, diabetic enteropathy, diabetic neuropathy including diabetic neuralgia and the like.

In one embodiment, the thrombosis is a secondary and/or local thrombosis; the thrombosis-related disease is a secondary and/or local thrombosis-related disease.

In one embodiment, plasminogen has a sequence identity of at least 80%, 85%, 90%, 95%, 96%, 97%, 98%, or 99% with SEQ ID No. 2, 6, 8, 10, or 12, and still has plasminogen activity. In one embodiment, the plasminogen is a protein that added, deleted, and/or substituted 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid based on SEQ ID No. 2, 6, 8, 10, or 12, and still has plasminogen activity. In one embodiment, plasminogen is a protein that comprises a plasminogen active fragment and still has plasminogen activity. In one embodiment, the plasminogen is selected from the group consisting of Glu-plasminogen, Lys-plasminogen, mini-plasminogen, micro-plasminogen, δ-plasminogen, or any combination thereof. In one embodiment, the plasminogen is a conservatively substituted variant selected from the variants of Glu-plasminogen, Lys-plasminogen, mini-plasminogen, δ-plasminogen or micro-plasminogen. In one embodiment, the plasminogen is a human natural plasminogen, such as orthologs of plasminogen shown in SEQ ID No.2, for example, plasminogen orthologs from primates or rodents, such as plasminogen orthologs from gorillas, rhesus monkeys, rats, cows, horses, and dogs. Most preferably, the plasminogen of the present invention has the amino acid sequence shown as SEQ ID No.2, 6, 8, 10, or 12. In one embodiment, the plasminogen is administered systemically or topically, preferably by the following routes: superficial, intravenous, intramuscular, subcutaneous, inhalation, intraspinal, local injection, intra-articular injection or via the rectum. In one embodiment, the topical administration is performed by applying a plasminogen-containing dressing and/or catheter to the thrombus area.

In one embodiment, the plasminogen is administered in combination with a suitable polypeptide carrier or stabilizer. In one embodiment, the plasminogen is administered at a dose of 0.0001-2000 mg/kg, 0.001-800 mg/kg, 0.01-600 mg/kg, 0.1-400 mg/kg, 1-200 mg/kg, 1-100 mg/kg, 10-100 mg/kg (calculated per kilogram of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$, 10-100 mg/cm$^2$ (calculated per square centimeter of body surface area) per day, preferably repeat at least once, preferably at least daily. In the case of topical application, the above dosage can be further adjusted according to the situation.

The above plasminogen can be administered alone or in combination with other drugs for preventing and/or treating other diseases associated with pathological thrombosis. The other drugs include, for example, cardiovascular disease therapeutic drugs, arrhythmia therapeutic drugs, diabetes therapeutic drugs, etc.

In another aspect, the present invention relates to the use of plasminogen in the preparation of drugs, articles of manufacture, kits for preventing and/or eliminating arterial and venous thrombosis in a subject. The invention also relates to a method for preparing a drug, article of manufacture and kit for preventing and/or eliminating arterial and venous thrombosis in a subject, which comprises preparing the plasminogen and a pharmaceutically acceptable carrier together into a drug, an article of manufacture and a kit for preventing and/or eliminating arterial and venous thrombosis in a subject. In one embodiment, the thrombus comprises a fresh thrombus (acute thrombus) and old thrombus (chronic thrombus). In one embodiment, the thrombosis is a thrombosis caused by a blood system disease, a circulatory system disease, an autoimmune disease, a metabolic disorder, or an infectious disease. In one embodiment, the thrombosis is a large and/or small vascular thrombosis, and/or microvascular thrombosis, secondary to diabetes. In one embodiment, the thrombosis is a thrombosis caused by large and/or small vascular lesions.

In one aspect, the present invention relates to a use of plasminogen in the preparation of a drug, an article of manufacture or a kit for preventing and/or eliminating pathological thrombosis in a subject, and the use of plasminogen in the preparation of a drug, an article of manufacture or a kit for preventing and/or treating thrombosis-related diseases in a subject. The invention also relates to a method for preparing a drug, an article of manufacture or a kit for preventing and/or eliminating pathological thrombosis in a subject, which comprises preparing a plasminogen and a pharmaceutically acceptable carrier together into the drug, article of manufacture or kit, or, a method for preparing a drug, an article of manufacture or a kit for preventing and/or treating thrombosis-related diseases in a subject, which comprises preparing a plasminogen and a pharmaceutically acceptable carrier together into the drug, article of manufacture or kit. The thrombus is a fresh thrombus and/or an old thrombus. The thrombosis-related disease is a fresh thrombus and/or an old thrombus-induced disease. The subject is a mammal, preferably a human.

In one embodiment, the subject has a low level of plasmin or plasminogen. Specifically, the low level of plasmin or plasminogen is innate, secondary, and/or local.

In one embodiment, the above thrombosis is a venous thrombosis and/or arterial thrombosis. The thrombosis-related diseases include pancreatitis and cirrhosis caused by portal vein thrombosis; renal embolism caused by renal vein thrombosis; systemic sepsis, pulmonary embolism, cerebral thrombosis caused by internal jugular vein thrombosis;

organ infarctions caused by arterial thrombosis, including but not limited to: cerebral infarction, myocardial infarction, thrombotic stroke, atrial fibrillation, unstable angina pectoris, intractable angina pectoris, transient ischemic attack, pulmonary embolism, diabetes-induced large and/or small vascular embolism, etc.

In one embodiment, the thrombosis-related diseases are diabetic nephropathy, diabetic retinopathy, diabetic liver disease, diabetic heart disease, diabetic enteropathy, diabetic neuropathy including diabetic neuralgia and the like.

In one embodiment, the thrombosis is a secondary and/or local thrombosis; the thrombosis-related disease is a secondary and/or local thrombosis-related disease.

In one embodiment, plasminogen has a sequence identity of at least 80%, 85%, 90%, 95%, 96%, 97%, 98%, or 99% with SEQ ID No.2, 6, 8, 10, or 12, and still has plasminogen activity. In one embodiment, plasminogen is a protein that added, deleted, and/or substituted 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid based on SEQ ID No. 2, 6, 8, 10, or 12, and still has plasminogen activity. In one embodiment, plasminogen is a protein that comprises a plasminogen active fragment and still has plasminogen activity. In one embodiment, the plasminogen is selected from the group consisting of Glu-plasminogen, Lys-plasminogen, mini-plasminogen, micro-plasminogen, δ-plasminogen, or any combination thereof. In one embodiment, the plasminogen is a conservatively substituted variant selected from the variants of Glu-plasminogen, Lys-plasminogen, mini-plasminogen, δ-plasminogen or micro-plasminogen. In one embodiment, the plasminogen is a human natural plasminogen, such as orthologs of plasminogen shown in SEQ ID No.2, for example, plasminogen orthologs from primates or rodents, such as plasminogen orthologs from gorillas, rhesus monkeys, rats, cows, horses, and dogs. Most preferably, the plasminogen of the present invention has the amino acid sequence shown as SEQ ID No.2, 6, 8, 10, or 12. In one embodiment, the plasminogen is administered systemically or topically, preferably by the following routes: superficial, intravenous, intramuscular, subcutaneous, inhalation, intraspinal, local injection, intra-articular injection or via the rectum. In one embodiment, the topical administration is performed by applying a plasminogen-containing dressing and/or catheter to the thrombus area.

The above plasminogen can be administered alone or in combination with other drugs for the treatment of other diseases associated with pathological thrombosis. The other drugs include, for example, cardiovascular disease therapeutic drugs, arrhythmia therapeutic drugs, diabetes therapeutic drugs, etc.

In one embodiment, the plasminogen is administered in combination with a suitable polypeptide carrier or stabilizer. In one embodiment, the plasminogen is administered at a dose of 0.0001-2000 mg/kg, 0.001-800 mg/kg, 0.01-600 mg/kg, 0.1-400 mg/kg, 1-200 mg/kg, 1-100 mg/kg, 10-100 mg/kg (calculated per kilogram of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$, 10-100 mg/cm$^2$ (calculated per square centimeter of body surface area) per day, preferably repeat at least once, preferably at least daily. In the case of topical application, the above dosage can be further adjusted according to the situation.

In another aspect, the present invention relates to a plasminogen for preventing and/or eliminating arterial and venous thrombosis in a subject, and a pharmaceutical composition comprising a plasminogen for preventing and/or eliminating arterial and venous thrombosis in a subject. In one embodiment, the thrombus comprises fresh thrombus and old thrombus. In one embodiment, the thrombosis is a thrombosis caused by a blood system disease, a circulatory system disease, an autoimmune disease, a metabolic disorder disease, or an infectious disease. In one embodiment, the thrombosis is a large and/or small vascular thrombosis, and/or microvascular thrombosis, secondary to diabetes. In one embodiment, the thrombosis is a thrombosis caused by large and/or small vascular lesions. In one aspect, the present invention relates to a plasminogen for preventing and/or treating thrombosis-related diseases, and a pharmaceutical composition comprising a plasminogen for preventing and/or treating thrombosis-related diseases. The above thrombus is a fresh thrombus and/or an old thrombus, and the thrombosis-related disease is a fresh thrombus and/or an old thrombus-induced disease. In one embodiment, the above thrombosis is a venous thrombosis and/or arterial thrombosis. The thrombosis-related diseases include pancreatitis and cirrhosis caused by portal vein thrombosis; renal embolism caused by renal vein thrombosis; systemic sepsis, pulmonary embolism, cerebral thrombosis caused by internal jugular vein thrombosis; organ infarctions caused by arterial thrombosis, including but not limited to: cerebral infarction, myocardial infarction, thrombotic stroke, atrial fibrillation, unstable angina pectoris, intractable angina pectoris, transient ischemic attack, pulmonary embolism, diabetes-induced large and/or small vascular embolism, etc.

In one embodiment, the thrombosis-related diseases are diabetic nephropathy, diabetic retinopathy, diabetic liver disease, diabetic heart disease, diabetic enteropathy, diabetic neuropathy including diabetic neuralgia and the like.

In one embodiment, the above thrombosis is an innate, secondary and/or local thrombosis; the above thrombosis-related disease is an innate, secondary and/or local thrombosis-related disease.

In one embodiment, plasminogen has a sequence identity of at least 80%, 85%, 90%, 95%, 96%, 97%, 98%, or 99% with SEQ ID No.2, 6, 8, 10, or 12, and still has plasminogen activity. In one embodiment, plasminogen is a protein that added, deleted, and/or substituted 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid based on SEQ ID No. 2, 6, 8, 10, or 12, and still has plasminogen activity. In one embodiment, plasminogen is a protein that comprises a plasminogen active fragment and still has plasminogen activity. In one embodiment, the plasminogen is selected from the group consisting of Glu-plasminogen, Lys-plasminogen, mini-plasminogen, micro-plasminogen, δ-plasminogen, or any combination thereof. In one embodiment, the plasminogen is a conservatively substituted variant selected from the variants of Glu-plasminogen, Lys-plasminogen, mini-plasminogen, δ-plasminogen or micro-plasminogen. In one embodiment, the plasminogen is a human natural plasminogen, such as orthologs of plasminogen shown in SEQ ID No.2, for example, plasminogen orthologs from primates or rodents, such as plasminogen orthologs from gorillas, rhesus monkeys, rats, cows, horses, and dogs. Most preferably, the plasminogen of the present invention has the amino acid sequence shown as SEQ ID No.2, 6, 8, 10, or 12. In one embodiment, the plasminogen is administered systemically or topically, preferably by the following routes: superficial, intravenous, intramuscular, subcutaneous, inhalation, intraspinal, local injection, intra-articular injection or via the rectum. In one embodiment, the topical administration is performed by applying a plasminogen-containing dressing and/or catheter to the thrombus area.

In one embodiment, the plasminogen is administered in combination with a suitable polypeptide carrier or stabilizer. In one embodiment, the plasminogen is administered at a dose of 0.0001-2000 mg/kg, 0.001-800 mg/kg, 0.01-600 mg/kg, 0.1-400 mg/kg, 1-200 mg/kg, 1-100 mg/kg, 10-100 mg/kg (calculated per kilogram of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$, 10-100 mg/cm$^2$ (calculated per square centimeter of body surface area) per day, preferably repeat at least once, preferably at least daily. In the case of topical application, the above dosage can be further adjusted according to the situation.

In another aspect, the present invention relates to an article of manufacture or a kit comprising a plasminogen for preventing and/or eliminating an arterial and venous thrombosis in a subject. In one embodiment, the thrombus comprises fresh thrombus and old thrombus. In one embodiment, the thrombosis is a thrombosis caused by a blood system disease, a circulatory system disease, an autoimmune disease, a metabolic disorder disease, or an infectious disease. In one embodiment, the thrombosis is a large and/or small vascular thrombosis, and/or microvascular thrombosis, secondary to diabetes. In one embodiment, the thrombosis is a thrombosis caused by large and/or small vascular lesions. In one embodiment, the article or kit comprises a container containing an effective amount of plasminogen. Further, the article or kit also includes a container containing one or more other drugs, wherein the other drug is a therapeutic drug for other diseases accompanying thrombosis. The kit can also comprise instructions for use, indicating that the plasminogen can be used to prevent and/or treat the arterial and venous thrombosis, or thrombosis-related diseases, and can further illustrate that the plasminogen can be administered before, simultaneously with, and/or after the administration of other drug(s). In one embodiment, the other drug may be a cardiovascular disease therapeutic drug, an arrhythmia therapeutic drug, a diabetes therapeutic drug, or the like, to treat other diseases accompanied with pathological thrombosis. In specific embodiments, the thrombus is a fresh thrombus and/or an old thrombus, and the thrombosis-related disease is a fresh thrombus-induced disease and/or an old thrombus-induced disease.

In one embodiment, the above thrombosis is a venous thrombosis and/or arterial thrombosis. The thrombosis-related diseases include pancreatitis and cirrhosis caused by portal vein thrombosis; renal embolism caused by renal vein thrombosis; systemic sepsis, pulmonary embolism, cerebral thrombosis caused by internal jugular vein thrombosis; organ infarctions caused by arterial thrombosis, including but not limited to: cerebral infarction, myocardial infarction, thrombotic stroke, atrial fibrillation, unstable angina pectoris, intractable angina pectoris, transient ischemic attack, pulmonary embolism, diabetes-induced large and/or small vascular embolism, etc.

In one embodiment, the thrombosis-related diseases are diabetic nephropathy, diabetic retinopathy, diabetic liver disease, diabetic heart disease, diabetic enteropathy, diabetic neuropathy including diabetic neuralgia and the like.

In one embodiment, the above thrombosis is an innate, secondary and/or local thrombosis; the above thrombosis-related disease is an innate, secondary and/or local thrombosis-related disease.

In one embodiment, plasminogen has a sequence identity of at least 80%, 85%, 90%, 95%, 96%, 97%, 98%, or 99% with SEQ ID No.2, 6, 8, 10, or 12, and still has plasminogen activity. In one embodiment, plasminogen is a protein that added, deleted, and/or substituted 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid based on SEQ ID No. 2, 6, 8, 10, or 12, and still has plasminogen activity. In one embodiment, plasminogen is a protein that comprises a plasminogen active fragment and still has plasminogen activity. In one embodiment, the plasminogen is selected from the group consisting of Glu-plasminogen, Lys-plasminogen, mini-plasminogen, micro-plasminogen, δ-plasminogen, or any combination thereof. In one embodiment, the plasminogen is a conservatively substituted variant selected from the variants of Glu-plasminogen, Lys-plasminogen, mini-plasminogen, δ-plasminogen or micro-plasminogen. In one embodiment, the plasminogen is a human natural plasminogen, such as orthologs of plasminogen shown in SEQ ID No.2, for example, plasminogen orthologs from primates or rodents, such as plasminogen orthologs from gorillas, rhesus monkeys, rats, cows, horses, and dogs. Most preferably, the plasminogen of the present invention has the amino acid sequence shown as SEQ ID No.2, 6, 8, 10, or 12.

In one embodiment, the subject has a low level of plasmin or plasminogen. Specifically, the low level of plasmin or plasminogen is innate, secondary, and/or local.

The present invention specifically covers all combinations of technical features that fall within the embodiments of the present invention, and these combined technical solutions have been explicitly disclosed in the present application, just as the above technical solutions have been individually and explicitly disclosed. In addition, the present invention also explicitly covers all sub-combinations of the various embodiments and the elements thereof, and is disclosed herein as if each such sub-combination is individually and explicitly disclosed herein.

DETAILED DESCRIPTION OF THE INVENTION

1. Definition

A "thrombus" is the product of the coagulation process. The coagulation process is the defense mechanism that the body maintains the integrity of the closed high pressure circulatory system. Under normal circumstances, the process should remain inactivated, but when the tissue is damaged, the mechanism needs to be activated immediately to reduce blood extravasation. When blood vessels are damaged, fibrinogen dissolved in plasma under the action of thrombin will eventually be converted into fibrin polymers that are insoluble in water, and they will be intertwined with each other to form a net which traps blood cells within it to form a blood clot, completing the coagulation process. In this process, the ratio of the size of the blood clot to the wound is crucial. Therefore, there should be a balance between molecules that initiate clot formation (fibrin, thrombin) and molecules that dissolve blood clots (plasmin, plasminogen activator, etc.). But in the pathological process, the disruption of this balance will result in excess blood clot formation molecules, which in turn will form thrombus, which is a "pathological thrombus".

In the human body, thrombosis can occur at any location with blood flow and is currently divided into two major categories: venous thrombosis and arterial thrombosis. Venous thrombosis is caused by a blood clot produced in the vein. The most common type of venous thrombosis is: deep vein thrombosis (DVT), which usually affects the limb veins, such as the femoral vein, resulting in pain and swelling of the affected area; portal vein thrombosis, which can affect the hepatic portal vein, then leading to pancreatitis, cirrhosis, diverticulitis or cholangiocarcinoma; renal vein thrombosis, leading to renal embolism; internal jugular vein thrombosis, which can cause various complications such as systemic sepsis and pulmonary embolism; cerebral vein thrombosis, leading to headaches, visual anomaly, strokes and other symptoms in patients. Arterial thrombosis may lead to infarction of almost any organ in the body. The diseases it causes include but are not limited to: cerebral infarction, myocardial infarction, thrombotic stroke, atherosclerotic disease, unstable angina, intractable angina, transient ischemic attack, pulmonary embolism, etc.

Thrombosis-related diseases are diseases caused by two pathological processes of thrombosis and thromboembolism. The term thrombosis-related disease of the present invention specifically covers all diseases caused by thrombosis and thromboembolism.

Thrombosis refers to a pathological process where elements of blood form emboli in blood vessels (mostly small blood vessels) under certain conditions, which results in partial or complete blockage of the blood vessels and blood supply disorders in corresponding sites. According to the composition of thrombus, thrombosis can be divided into platelet thrombosis, red blood cell thrombosis, fibrin thrombosis, mixed thrombosis, etc. According to the type of blood vessels, thrombosis can be divided into arterial thrombosis, venous thrombosis and capillary thrombosis.

Thromboembolism is a pathological process that occurs when a thrombus falls off from the site of formation and partially or completely blocks certain blood vessels during movement with blood flow, causing ischemia, hypoxia, necrosis (arterial thrombosis), congestion, and edema (venous thrombosis) in the corresponding tissues and (or) organs.

Deep vein thrombosis of lower extremities is the most common form of venous thrombosis which is commonly seen in deep veins such as popliteal veins, femoral veins, mesenteric veins, portal veins, etc. It is mostly red blood cell thrombus or fibrin thrombus. The main manifestations are: (1) local swelling and pain of thrombosis; (2) blood reflux disorder at distal thrombosis, such as distal edema, pain, skin color change, ascites, etc.; (3) related organ dysfunction caused by embolization of blood vessels after clot detachment, such as pulmonary infarction symptoms, signs, etc.

Arterial thrombosis is more common in coronary arteries, cerebral arteries, mesenteric arteries, and limb arteries, the type of which is mostly platelet thrombosis in the early stages, followed by fibrin thrombosis. The clinical manifestations are: (1) mostly sudden onset, with severe local pain, such as angina, abdominal pain, severe physical pain, etc.; (2) organ, tissue structure and function abnormalities caused by ischemia and hypoxia in relevant blood supply sites, such as myocardial infarction, heart failure, cardiogenic shock, arrhythmia, disturbance of consciousness and hemiplegia, etc.; (3) cerebral embolism, renal embolism, spleen embolism and other related symptoms and signs caused by breaking off of clots; (4) clinical manifestations caused by ischemic necrosis of blood supply, such as fever, etc.

Capillary thrombosis is common in DIC, TTP, and hemolytic uremic syndrome (HUS). The clinical manifestations are often lack of specificity, and are mainly mucocutaneous embolic necrosis, microcirculation failure and organ dysfunction.

"Diabetes mellitus" is a syndrome of metabolic disorder of a series of substances such as sugar, protein, fat, water and electrolytes, triggered by various pathogenic factors such as genetic factors, immune disorders, microbial infections and their toxins, free radical toxins, mental factors, etc., which act on the body resulting in the decline of pancreas islet function and insulin resistance, etc. It is clinically characterized by high blood sugar.

"Diabetic complications" are impairments or dysfunctions of other organs or tissues of the body caused by poor blood glucose control during diabetes, including liver, kidney, heart, retina, nervous system damage or dysfunction, and the like. According to the statistics of the World Health Organization, there are more than 100 complications of diabetes, which is currently known to have the most complications. These complications of diabetes are mainly due to the damage of the major blood vessels, small blood vessels and micro-vessels of various organs of the patient.

"Diabetic macroangiopathy" mainly refers to atherosclerosis in aorta and various organ arteries. Its pathogenesis includes the following aspects: (1) sustained hyperglycemia increases blood viscosity and coagulation, which in turn causes arterial vascular elasticity to weaken and even lose; (2) abnormal lipid metabolism, which promotes the accumulation of cholesterol and cholesteryl esters in the cells, leading to the occurrence and development of atherosclerosis; (3) arterial wall endothelial cell injury. Hemodynamic changes make the blood mechanically long-term impact on the vascular endothelium, causing endothelial damage, then resulting in adhesion of platelets, fibrin, etc. at the site of injury to form thrombosis, and can further lead to inflammation; (4) the increase of glycoproteins involved in the coagulation mechanism promotes the aggregation of platelets and fibrin and their adhesion to the damaged subendothelial layer, and causes a decrease in solvency and further thrombus formation.

"Diabetic microangiopathy" refers to microvascular disease caused by different degrees of abnormalities in the microcirculation of various organs or tissues of the body of a diabetic patient. The process of formation of microangiopathy is roughly as follows: microcirculation functional changes, endothelial injury, thickening of basement membrane, increased blood viscosity, aggregation of red blood cells, platelet adhesion and aggregation, and finally resulting in microthrombosis and/or microvascular occlusion.

The above two "diabetic vasculopathy" result in local vascular damage, poor blood flow, cell hypoxia, clot formation, thrombosis, and inflammation in tissues or organs, and further affect the function of surrounding tissues and organs, leading to diabetic complications such as diabetic heart disease, diabetic enteropathy, diabetic nephropathy, diabetic retinopathy, diabetic liver disease and diabetic neuropathy.

"Diabetic nephropathy" is a diabetic microvascular complication, which mainly refers to diabetic glomerulosclerosis, a glomerular lesion mainly based on vascular lesions. Its characteristics include proteinuria, hypertension, edema, glomerulosclerosis, vascular structural changes, and tubulointerstitial disease. The first clinical evidence of diabetic nephropathy is usually the presence of albuminuria in the urine, such as microalbuminuria or macroalbuminuria.

"Diabetic neuropathy" is caused by diabetes-induced nervous system damage, including sensory nerve damage, motor nerve damage, and autonomic nerve damage, in which sensory nerve damage is usually more serious. Common symptoms include but are not limited to: physical pain, hypoesthesia, numbness, burning, coldness, and diabetic neuropathic pain which includes but not limited to spontaneous pain, hypoalgesia and hyperalgesia induced by diabetic complications.

"Diabetic neuralgia" is the most common form of diabetic neuropathy, usually caused by impaired diabetic sensory nerves. The main pain is usually accompanied by loss of temperature and tactility. Pain occurs most often in the lower limbs, but also in the upper limbs and torso, and generally it can be divided into peripheral and central nervous pain. Peripheral nerve pain is caused by damage to peripheral nerves, while central nervous pain is caused by damage to the central nervous system and/or spinal cord.

"Diabetic liver injury" refers to a pathological change in which liver histology and function are changed due to diabetes. It is mainly caused by diabetes-induced macrovascular and microvascular lesions. It is known that liver damage caused by diabetes includes: abnormalities of liver enzymology, which can cause carbon dioxide accumulation in liver cells, acidosis, reduced oxygen supply, increased oxygen consumption, increased liver transaminase activity, bilirubin metabolism disorder, and severe cases can cause liver cell necrosis; fatty liver, in all causes of which diabetes accounts for the third place, and 21% to 78% of diabetic patients have fatty liver; hepatitis, cirrhosis and liver cancer, in which the prevalence of viral hepatitis in diabetic patients is about 2-4 times that of normal people, and the incidence of primary liver cancer is about 4 times that of normal people.

Clinically, liver disease and its associated symptoms caused by diabetes include but are not limited to: liver enzymology abnormalities, liver discomfort and tenderness, hepatomegaly, splenomegaly, hepatosplenomegaly, hepatitis, fatty liver, cholangitis, cirrhosis, hepatic necrosis, liver cancer, etc.

"Diabetic cardiovascular disease" refers to a pathological change in which histology and function of the cardiovascular system are changed due to diabetes, which is one of the most common diabetic complications, mainly caused by diabetes-induced macrovascular and microvascular lesions. Among them, the patient's clinical manifestations include abnormal electrocardiogram, enlarged heart, arrhythmia, angina pectoris, painless myocardial infarction and heart failure. According to statistics, about 70% to 80% of diabetics eventually die of cardiovascular complications.

"Diabetic retinopathy" refers to a pathological change in which the retinal histology and function are changed due to diabetes, mainly caused by diabetes-induced macrovascular and microvascular lesions caused by diabetes. Diabetic retinopathy is the most common diabetic eye disease, and often leads to vision loss or blindness. According to statistics, 50% of diabetic patients will have this disease within about 10 years of the disease course, and 80% for more than 15 years. The heavier the condition of diabetes, the older it is, the higher the incidence of diabetes is.

When the thrombus tissue of the patient is examined by CT or MRI techniques, the lesion is seen as fresh or old thrombus. The first lesion is a fresh lesion during the acute attack period. The ischemic center of the lesion is partially necrotic, and some of the lesions are likely to recover, with surrounding area not affected. The purpose of treatment at this time should be mainly to prevent the expansion of the "central infarct zone". The old thrombus is the complete necrosis of the tissue ischemic center. The purpose of the treatment should be to make the function of the surrounding tissue of the infarct zone continue to be improved. There is a high risk of recurrence of old thrombus, so treatment and prevention are equally important for patients with old thrombosis, and the high recurrence rate should be reduced while the degree of symptoms are reduced. Many current thrombolytic drugs are effective for the treatment of fresh thrombus in the acute phase, but they are less effective for the treatment of old thrombus.

"Plasmin" is a very important enzyme that exists in the blood and can hydrolyze fibrin clots into fibrin degradation products and D-dimers.

"Plasminogen" is the zymogen form of plasmin and is composed of 810 amino acids calculated from the amino acid sequence (SEQ ID No. 4) of natural human plasminogen containing a signal peptide, based on the sequence in swiss prot, with a molecular weight of approximately 92 kD. It is a glycoprotein synthesized mainly in the liver and capable of circulating in the blood, and the cDNA sequence encoding the amino acid sequence is shown in SEQ ID No. 3. Full-length PLG contains seven domains: a serine protease domain at C-terminal, a Pan Apple (PAp) domain at N-terminal and five Kringle domains (Kringle1-5). Referring to the sequence in swiss prot, its signal peptide includes residues Met1-Gly19, PAp includes residues Glu20-Va198, Kringle1 includes residues Cys103-Cys181, Kringle2 includes residues Glu184-Cys262, Kringle3 includes residues Cys275-Cys352, Kringle4 includes residues Cys377-Cys454 and Kringle5 includes residues Cys481-Cys560. According to NCBI data, the serine protease domain includes residues Va1581-Arg804.

Glu-plasminogen is a natural full-length plasminogen and consists of 791 amino acids (not including the 19 amino acid signal peptide). The cDNA sequence encoding the sequence is shown as SEQ ID No. 1 and its amino acid sequence is shown as SEQ ID No.2. In vivo, there is Lys-plasminogen which is formed by hydrolysis of amino acids 76-77 of Glu-plasminogen, as shown in SEQ ID No. 6, and the cDNA sequence encoding the amino acid sequence is shown as SEQ ID No. 5. δ-plasminogen is a fragment of full-length plasminogen that lacks the Kringle2-Kringle5 structure, only containing Kringle1 and serine protease domains[28, 29]. The amino acid sequence of δ-plasminogen has been reported in the literature (SEQ ID No. 8)[30], and the cDNA sequence encoding the amino acid sequence is shown as SEQ ID No. 7.

Mini-plasminogen is composed of Kringle5 and serine protease domain and it has been reported in the literature that it includes residues Va1443-Asn791 (with the Glu residue of Glu-plg sequence that does not contain a signal peptide as starting amino acid)[31]. Its amino acid sequence is shown as SEQ ID No. 10, and the cDNA sequence encoding this amino acid sequence is shown as SEQ ID No. 9.

Micro-plasminogen only contains a serine protease domain, and its amino acid sequence has been reported in the literature to include residues Ala543-Asn791 (with the Glu residue of a Glu-plg sequence that does not contain a signal peptide as starting amino acid)[32]. Patent CN102154253A also reported that its sequence includes residues Lys531-Asn791 (with the Glu residue of a Glu-plg sequence that does not contain a signal peptide as starting amino acid). The sequence of the present patent application refers to the patent document CN102154253A. Its amino acid sequence is shown as SEQ ID No. 12, and the cDNA sequence encoding this amino acid sequence is shown as SEQ ID No. 11.

In the present invention, "plasmin" is used interchangeably with "fibrinolysin" and "fibrinoclase", and the terms have the same meaning; and "plasminogen" is used interchangeably with "fibrinolytic zymogen" and "fibrinoclase zymogen", and the terms have the same meaning.

The "fresh thrombus" and "acute thrombus" of the present invention can be used interchangeably; "old thrombus" and "chronic thrombus" can be used interchangeably.

In the course of circulation, plasminogen adopts closed inactive conformation, but when bound to the thrombus or cell surface, it is converted to an active plasmin in an open conformation mediated by plasminogen activator (PA). Active plasmin can further hydrolyze fibrin clots to fibrin degradation products and D-dimer, which in turn dissolves clots. The PAp domain of plasminogen contains an important determinant that maintains plasminogen in an inactive closed conformation, whereas the KR domain is capable of binding to lysine residues present on receptors and substrates. A variety of enzymes are known to be capable of acting as plasminogen activators, including: tissue plasminogen activator (tPA), urokinase plasminogen activator (uPA), kallikrein, blood coagulation factor XII (Hageman factor), etc.

"Plasminogen active fragment" refers to an active fragment in a plasminogen protein capable of binding to a target sequence in a substrate and exerting a proteolytic function. The technical solution of the present invention involving plasminogen covers a technical solution for replacing plasminogen with an active fragment of plasminogen. The plasminogen active fragment of the present invention is a protein comprising a serine protease domain of plasminogen. Preferably, the plasminogen active fragment of the present invention comprises the protein of SEQ ID NO. 14, or an amino acid sequence having at least 80%, 90%, 95%, 96%, 97%, 98%, 99% homology with the SEQ ID NO. 14. Therefore, the plasminogen of the present invention includes a protein comprising the plasminogen active fragment and still retaining the plasminogen activity.

At present, methods for the determination of plasminogen and its activity in blood include: detection of tissue plasminogen activator activity (t-PAA), detection of plasma tissue plasminogen activator antigen (t-PAAg), detection of plasma tissue plasminogen activity (plgA), detection of plasma tissue plasminogen antigen (plgAg), detection of plasma tissue plasminogen activator inhibitor activity, detection of plasma tissue plasminogen activator inhibitor antigen, detection of plasma plasmin-antiplasmin complex (PAP). The most commonly used detection method is the chromogenic substrate method: adding streptokinase (SK) and chromogenic substrate to the tested plasma; PLG in the tested plasma is converted to PLM under the action of SK, the latter acting on the chromogenic substrate, and then measured with a spectrophotometer; increased absorbance is proportional to plasminogen activity. In addition, the plasminogen activity in blood can also be measured by immunochemistry, gel electrophoresis, immunoturbidimetry, radioimmunoassay, and the like.

"Orthologs" refers to homologs between different species, including both protein homologs and DNA homologs, and are also known as orthologous homologs and vertical homologs. It specifically refers to proteins or genes that have evolved from the same ancestral gene in different species. The plasminogen of the present invention includes human natural plasminogen, and also includes orthologues or orthologs of plasminogens derived from different species and having plasminogen activity.

"Conservative substitutional variant" refers to a change in one of the given amino acid residues without altering the overall conformation and function of the protein or enzyme, including but not limited to the replacement of amino acids in the amino acid sequence of a parent protein with amino acids of similar properties (e.g. acidic, basic, hydrophobic, etc.). Amino acids with similar properties are well known. For example, arginine, histidine and lysine are hydrophilic basic amino acids and are interchangeable. Similarly, isoleucine is a hydrophobic amino acid that can be replaced by leucine, methionine or valine. Therefore, the similarity of two proteins or amino acid sequences of similar functions may be different. For example, 70% to 99% similarity (identity) based on the MEGALIGN algorithm. A "conservatively substituted variant" also includes a polypeptide or enzyme having amino acid identity of 60% or more, preferably 75% or more, more preferably 85% or more, even more preferably 90% or more as determined by the BLAST or FASTA algorithm, and having the same or substantially similar properties or functions as the natural or parent protein or enzyme.

"Isolated" plasminogen refers to plasminogen protein isolated and/or recovered from its natural environment. In some embodiments, the plasminogen will be purified (1) to greater than 90%, greater than 95%, or greater than 98% purity (by weight) as determined by the Lowry method, for example, over 99% (by weight), (2) to a degree sufficient to obtain at least 15 residues of the N-terminal or internal amino acid sequence using a spinning cup sequencer, or (3) to homogeneity, the homogeneity determined by sodium dodecyl sulfate-polyacrylamide gel electrophoresis (SDS-PAGE) using Coomassie blue or silver staining under reducing or non-reducing conditions. Isolated plasminogen also includes plasminogen prepared from recombinant cells by bioengineering techniques and separated by at least one purification step.

The terms "polypeptide", "peptide", and "protein" are used interchangeably herein and refer to a polymeric form of an amino acid of any length. It may include genetically encoded and non-genetically encoded amino acids, chemically or biochemically modified or derivatized amino acids, and polypeptides having a modified peptide backbone. The term includes fusion proteins including, but not limited to, fusion proteins having heterologous amino acid sequences, fusions having heterologous and homologous leader sequences (with or without N-terminal methionine residues), etc.

The "amino acid sequence identity percentage (%)" with respect to the reference polypeptide sequence is defined as the percentage of amino acid residues in the candidate sequence that are identical to those in the reference polypeptide sequence, when gaps are introduced as necessary to achieve maximum percentage sequence identity and no conservative substitutions are considered as part of sequence identity. Comparisons for purposes of determining percent amino acid sequence identity can be achieved in a variety of ways within the skill of the art, for example using publicly available computer software such as BLAST, BLAST-2, ALIGN or Megalign (DNASTAR) software. Those skilled in the art can determine appropriate parameters for aligning sequences, including any algorithms needed to achieve maximum contrast over the full length of the sequences being compared. However, for purposes of the present invention, the amino acid sequence identity percent value is generated using the sequence comparison computer program ALIGN-2.

In the case of comparing amino acid sequences using ALIGN-2, the % amino acid sequence identity of a given amino acid sequence A relative to a given amino acid sequence B (alternatively, it can be expressed as a given amino acid sequence A having or containing a certain % amino acid sequence identity with respect to, with, or for a given amino acid sequence B) is calculated as follows:

$$\text{fraction } X/Y \text{ by } 100$$

Where X is the number of identically matched amino acid residues scored by the sequence alignment program ALIGN-2 in the A and B alignments of the program, and where Y is the total number of amino acid residues in B. It will be appreciated that where the length of amino acid sequence A is not equal to the length of amino acid sequence B, the % amino acid sequence identity of A relative to B will not equal the % amino acid sequence identity of B relative to A. Unless specifically stated otherwise, all % amino acid sequence identity values used herein were obtained using the ALIGN-2 computer program as described in the previous paragraph.

As used herein, the terms "treatment" and "treating" refer to obtaining a desired pharmacological and/or physiologic effect. The effect may be complete or partial prevention of a disease or its symptoms and/or partial or complete cure of the disease and/or its symptoms, and includes: (a) prevention of the disease from developing in a subject that may have a predisposition to the disease but has not been diagnosed as having the disease; (b) suppression of the disease, i.e., blocking its formation; and (c) alleviation of the disease and/or its symptoms, i.e., eliminating the disease and/or its symptoms.

The terms "individual", "subject" and "patient" are used interchangeably herein and refer to mammals, including, but not limited to, murine (rats and mice), non-human primates, humans, dogs, cats, hoofed animals (e.g., horses, cattle, sheep, pigs, goats) and so on.

"Therapeutically effective amount" or "effective amount" refers to an amount of plasminogen sufficient to achieve the described prevention and/or treatment of a disease when administered to a mammal or other subject to treat the disease. The "therapeutically effective amount" will vary depending on the plasminogen used, the condition of the subject to be treated, and/or the severity of its symptoms, as well as age, weight, and the like.

2. Preparation of Plasminogen of the Present Invention

Plasminogen can be isolated and purified from nature for further therapeutic uses and can also be synthesized by standard chemical peptide synthesis techniques. When chemically synthesizing polypeptides, they can be synthesized via liquid or solid phase. Solid phase peptide synthesis (SPPS) (in which the C-terminal amino acid of the sequence is attached to the insoluble support, followed by the sequential addition of the remaining amino acids in the sequence) is a method suitable for chemical synthesis of plasminogen. Various forms of SPPS such as Fmoc and Boc can be used to synthesize plasminogen. Techniques for solid-phase synthesis are described in Barany and Solid-Phase Peptide Synthesis; pages 3-284 in The Peptides: Analysis, Synthesis, Biology. Vol. 2: Special Methods in Peptide Synthesis, Part A., Merrifield, et al., J. Am. Chem. Soc., 85: 2149-2156 (1963); Stewart et al., Solid Phase Peptide Synthesis, 2nd ed. Pierce Chem. Co., Rockford, Ill. (1984); and Ganesan A. 2006 Mini Rev. Med Chem. 6:3-10 and Camarero J A et al., 2005 Protein Pept Lett. 12:723-8. Briefly, treating small insoluble porous beads with functional units on which peptide chains are built. After repeated cycles of coupling/deprotection, the attached solid free N-terminal amine is coupled to a single N-protected amino acid unit. Then, the unit is deprotected to expose new N-terminal amines that can be attached to other amino acids. The peptide remains immobilized on the solid phase, after which it is cut off.

Standard recombinant methods can be used to produce the plasminogen of the invention. For example, a nucleic acid encoding plasminogen is inserted into an expression vector so that it is operably linked to a regulatory sequence in the expression vector. Expression control sequences include, but are not limited to, promoters (e.g., naturally associated or heterologous promoters), signal sequences, enhancer elements, and transcription termination sequences. Expression regulation may be a eukaryotic promoter system in a vector, the vector that is capable of transforming or transfecting a eukaryotic host cell (e.g., COS or CHO cells). Once the vector is incorporated into a suitable host, the host is maintained under conditions suitable for high-level expression of the nucleotide sequence and collection and purification of plasminogen.

A suitable expression vector is usually replicated in the host organism as an episome or as an integral part of the host chromosomal DNA. In general, expression vectors contain a selection marker (e.g. ampicillin resistance, hygromycin resistance, tetracycline resistance, kanamycin resistance or neomycin resistance) to facilitate detection of those cells that are transformed exogenously with the desired DNA sequence.

*Escherichia coli* is an example of a prokaryotic host cell that can be used to clone a plasminogen-encoding polynucleotide. Other microbial hosts suitable for use include bacilli, such as *Bacillus subtilis* and other Enterobacteriaceae, such as *Salmonella*, *Serratia*, and various *Pseudomonas* species. In these prokaryotic hosts, expression vectors can also be generated which will usually contain expression control sequences (e.g., origins of replication) that are compatible with the host cell. In addition, there will be many known promoters, such as the lactose promoter system, the tryptophan (trp) promoter system, β-lactamase promoter system, or the promoter system from phage λ. A promoter usually controls expression, optionally in the case of manipulation of gene sequences, and has ribosome binding site sequences, etc., to initiate and complete transcription and translation.

Other microorganisms such as yeast can also be used for expression. Yeast (such as *S. cerevisiae*) and *Pichia* are examples of suitable yeast host cells, where appropriate vectors have expression control sequences (e.g. promoters), origins of replication, termination sequences, etc., as desired. Typical promoters include 3-phosphoglycerate kinase and other saccharolytic enzymes. The inducible yeast initiates promoters that specifically include enzymes derived from alcohol dehydrogenase, isocytochrome C, and responsible for the utilization of maltose and galactose.

In addition to microorganisms, mammalian cells (eg, mammalian cells cultured in in vitro cell culture) can also be used to express and produce the protein of the invention (eg, polynucleotides encoding the subject protein). See Winnacker, From Genes to Clones, VCH Publishers, N.Y., N.Y. (1987). Suitable mammalian host cells include CHO cell lines, various Cos cell lines, HeLa cells, myeloma cell lines, and transformed B cells or hybridomas. Expression vectors for these cells may contain expression control sequences such as origins of replication, promoters and enhancers (Queen et al., Immunol. Rev. 89:49 (1986)), and required processing information sites such as ribosome binding sites, RNA splice sites, polyadenylation sites, and transcription terminator sequences. Examples of suitable expression control sequences are promoters derived from white immunoglobulin genes, SV40, adenovirus, bovine papilloma virus, cytomegalovirus, and the like. See Co et al., J. Immunol. 148: 1149 (1992).

Once synthesized (in chemical or recombinant means), the plasminogen of the present invention may be purified according to standard procedures in the art, including ammonium sulfate precipitation, affinity column, column chromatography, high performance liquid chromatography (HPLC), gel electrophoresis, etc. The plasminogen is substantially pure, e.g., at least about 80% to 85% pure, at least about 85% to 90% pure, at least about 90% to 95% pure, or 98% to 99% pure, or purer, e.g., free of contaminants, the contaminants such as cell debris, macromolecules other than the plasminogen, and the like.

3. Pharmaceutical Formulations

A therapeutic formulation may be prepared by mixing a plasminogen of the desired purity with an optional pharmaceutical carrier, excipient, or stabilizer (Remington's Pharmaceutical Sciences, 16th edition, Osol, A. ed. (1980)) to form a lyophilized formulation or aqueous solution. Acceptable carriers, excipients, stabilizers are not toxic to the recipient at the doses and concentrations used and include buffers such as phosphates, citrates and other organic acids; antioxidants including ascorbic acid and methionine; preservatives (e.g. octadecyl dimethyl benzyl ammonium chloride; hexanediamine chloride; benzalkonium chloride, benzoxonium chloride; phenol, butanol or benzyl alcohol, alkyl p-hydroxybenzoate such as methyl or propyl p-hydroxybenzoate; catechol; resorcinol; cyclohexanol; 3-pentanol; m-cresol); low molecular weight polypeptides (less than about 10 residues); proteins such as serum albumin, gelatin or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agent such as EDTA; sugars such as sucrose, mannitol, fucose or sorbitol; salt-forming counterions such as sodium; metal complexes (e.g. zinc-protein complexes); and/or non-ionic surfactants such as TWEEN™, PLURONICS™ or polyethylene glycol (PEG).

Formulations of the invention may also contain more than one active compound required for the particular condition being treated, preferably those that are complementary in activity and have no side effects with one another. For example, anti-hypertensive drugs, anti-arrhythmic drugs, drugs for treating diabetes, etc.

The plasminogen of the present invention can be encapsulated in microcapsules prepared by techniques such as coacervation or interfacial polymerization, for example, can be placed in a colloidal drug delivery system (e.g. liposomes, albumin microspheres, microemulsions, nanoparticles and nanocapsules), or can be placed in hydroxymethyl cellulose or gel-microcapsules and poly-(methyl methacrylate) microcapsules in macroemulsions. These techniques are disclosed in Remington's Pharmaceutical Sciences 16th edition, Osol, A. Ed. (1980).

The plasminogen of the present invention for in vivo administration must be sterile. This can be easily achieved by filtration through a sterile filter before or after freeze drying and reconstitution.

The plasminogen of the present invention can prepare a sustained-release preparation. Suitable examples of sustained-release preparations include solid hydrophobic polymer semi-permeable matrices having a shape and containing glycoproteins, such as films or microcapsules. Examples of sustained release matrices include polyester, hydrogel (such as poly (2-hydroxyethyl-methacrylate) (Langer et al., J. Biomed. Mater. Res., 15: 167-277 (1981); Langer, Chem. Tech., 12:98-105 (1982)) or poly-(vinyl alcohol), polylactide (U.S. Pat. No. 3,773,919, EP 58,481), copolymer of L-glutamic acid and y ethyl-L-glutamic acid (Sidman, et al., Biopolymers 22:547 (1983)), non-degradable ethylene-vinyl acetate (Langer, et al., ibid.), or degradable lactic acid-glycolic acid copolymer such as Lupron Depot™ (injectable microspheres composed of lactic acid-glycolic acid copolymer and leuprolide acetate), and poly D-(−)-3-hydroxybutyric acid. Polymers such as ethylene vinyl acetate and lactic acid-glycolic acid can sustain release of molecules for more than 100 days, while some hydrogels release proteins for shorter periods of time. A rational strategy for protein stabilization can be designed based on relevant mechanisms. For example, if the mechanism of agglomeration is found to be the formation of intermolecular S—S bonds through the interchange of thiodisulfide bonds, stabilization can be achieved by modifying the thiol residues, lyophilizing from acidic solutions, controlling humidity, using suitable additives, and developing specific polymer matrix compositions.

4. Administration and Dosage

The pharmaceutical composition of the invention can be administered in different ways, for example by intravenous, intraperitoneal, subcutaneous, intracranial, intrathecal, intraarterial (such as via the carotid), intramuscular, intranasal, topical or intradermal administration or spinal cord or brain delivery. Aerosol formulations such as nasal spray formulations contain purified aqueous or other solutions of active agents with preservatives and isotonic agents. Such formulations are adjusted to a pH and isotonic state compatible with the nasal mucosa.

In some cases, the plasminogen pharmaceutical composition of the present invention may be modified or formulated in the following manner to provide its ability to cross the blood-brain barrier. Compositions of such plasminogen can be administered to individuals suffering from thrombosis and/or thrombosis-related diseases via a variety of enteral and parenteral routes of administration including oral, intravenous, and the like.

Preparations for parenteral administration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including salt water and buffer media. Parenteral vehicles include sodium chloride solution, Ringer dextrose, dextrose and sodium chloride, or fixed oils. Intravenous vehicles include liquid and nutrient supplements, electrolyte supplements, etc. Preservatives and other additives may also be present, for example, antimicrobials, antioxidants, chelating agents, and inert gases, etc.

In some embodiments, the plasminogen of the present invention is formulated with an agent that promotes crossing the blood-brain barrier. In some cases, the plasminogen of the present invention is fused directly or via a linker with a carrier molecule, peptide or protein that promotes crossing the blood-brain barrier. In some embodiments, the plasminogen of the present invention is fused to a polypeptide that binds to the endogenous blood-brain barrier (BBB) receptor. The polypeptide that binds to plasminogen and endogenous BBB receptor facilitates crossing the BBB. Suitable polypeptides that bind endogenous BBB receptors include antibodies, such as monoclonal antibodies, or their antigen-binding fragments that specifically bind to endogenous BBB receptors. Suitable endogenous BBB receptors include but are not limited to insulin receptors, transferrin receptors, lipoprotein receptors, and insulin-like growth factor receptors. In some cases, antibodies are encapsulated in liposomes. See, for example, U.S. Patent Publication No. 2009/0156498.

Medical staff will determine dose scheme based on various clinical factors. As known in the medical field, the dose of any patient depends on a variety of factors, including the patient's size, body surface area, age, the specific compound to be administered, sex, number and route of administration, overall health, and other medications administered simultaneously. The dose range of the pharmaceutical composition containing plasminogen of the present invention can be, for example, about 0.0001 to 2000 mg/kg, or about 0.001 to 500 mg/kg (e.g. 0.02 mg/kg, 0.25 mg/kg, 0.5 mg/kg, 0.75 mg/kg, 10 mg/kg, 50 mg/kg, etc.) of the subject's weight per day. For example, the dose can be 1 mg/kg body weight or 50 mg/kg body weight or in the range of 1-50 mg/kg, or at least 1 mg/kg. Dosages above or below this exemplary range are also covered, especially considering the above factors. The intermediate dose in the above range is also included in the scope of the present invention. Subjects can be administered such doses daily, on alternate days, weekly or on any other schedule determined by empirical analysis. Exemplary dose schedules include 1 to 10 mg/kg for consecutive days. In the drug administration process of the present invention, real-time evaluation and regular assessment of the therapeutic effect and safety of thrombosis and thrombosis-related diseases are required.

5. Therapeutic Efficacy and Safety Evaluation

Therapeutic Efficacy

The evaluation of the therapeutic efficacy of plasminogen is mainly performed by monitoring the following indicators:

(1) Thrombolysis rate after 1 week of treatment. For example, contrast agents can be injected through catheters to assess thrombolysis daily and score each blood vessel area. 0 stands for completely open, 1 for partial occlusion, and 2 for complete occlusion. According to the ratio that the total score before thrombolysis minus the total score after thrombolysis and divided by the total score before thrombolysis, thrombolysis is divided into different levels. The first level is <50%, the second level is 50% to 90%, and the third level is complete dissolution of the thrombus.

(2) Vascular patency rate after 6 months. For example, vascular patency rate can be evaluated by endoscopy, CT angiography analysis, color Doppler ultrasound, and the like. The effectiveness of the treatment is judged by whether there is a statistically significant increase in the percentage of vascular patency after treatment compared to before treatment.

(3) Vascular occlusion and/or venous reflux rate after 6 months. The improvement of the thrombolysis rate of drugs is judged by counting the decrease of vascular occlusion and/or venous reflux rate after treatment.

(4) Other assessment indicators. For example, endovascular echo changes, vascular wall thickness comparison, incidence of thrombotic sequelae after 2 years, etc. For example, vascular wall thickness and intraluminal echo can be assessed by gray-scale sonography, while iliac, femoral vein blood flow and femoral vein valve insufficiency can allow patients to adopt standing postures for evaluation with Doppler ultrasound.

Safety Evaluation

The safety after plasminogen drug therapy for thrombosis is evaluated. The evaluation mainly includes monitoring the incidence of adverse events after treatment. Severe bleeding, embolism, stroke, and death are generally defined as serious adverse events, while secondary bleeding and other minor symptoms of complications are defined as minor adverse events.

For safety evaluation, the most common adverse events are bleeding, such as intracranial hemorrhage (also known as hemorrhagic stroke, including subarachnoid hemorrhage, subdural hemorrhage, etc.). The said severe bleeding in the present invention generally refers to intracerebral bleeding or bleeding that is severe enough to cause death, surgery, cessation of treatment, or bleeding requiring blood transfusion, including "major hemorrhage" and "life-threatening hemorrhage". The secondary bleeding refers to bleeding around catheter sheath, and/or bleeding that can be stopped by changing the dose of a thrombolytic agent, anticoagulant or antiplatelet agent, or by compression. The terms "major hemorrhage" and "major bleeding event" specifically refer to hemoglobin content reduced by at least 2.0 g/L or blood transfusion of at least 2 units of blood, or symptomatic bleeding in a key site or organ. Bleeding events that are more severe than "major hemorrhage," i.e., a subcategory of major bleeding events, are called "life-threatening bleeding events," including fatal bleeding, symptomatic intracerebral hemorrhage, hemoglobin reduction of at least 5.0 g/L or blood transfusion requiring more than 4 units or bleeding requiring myocardial contraction agent or surgery.

In addition, for the assessment of patients with risk factors for major bleeding events, fine-tune their doses and follow-up monitor adverse events after their administration for at least 3 months, preferably 6 months or more, depending on the severity of the condition. The risk of major hemorrhage includes but is not limited to (1) age 75 years and older, (2) a history of previous bleeding events, and (3) having a reduced creatinine clearance that is less than 80 mL/minute or less than 50 mL/minute.

6. Articles of Manufacture or Kits

One embodiment of the present invention relates to an article or kit comprising plasminogen of the present invention that can be used to treat thrombosis. The article preferably includes a container, label or package insert. Suitable containers include bottles, vials, syringes, etc. The container can be made of various materials such as glass or plastic. The container contains a composition. The composition is effective for treating the disease or condition of the present invention and has a sterile entrance (for example, the container may be an intravenous solution bag or vial containing a stopper that can be pierced by a hypodermic injection needle). At least one active agent in the composition is plasminogen. The container or attached label indicates that the composition is used to treat the thrombosis and thrombosis-related diseases of the present invention. The article may further comprise a second container containing a pharmaceutically acceptable buffer, such as phosphate buffered saline, Ringer's solution, and glucose solution. It may further contain other substances required from a commercial and user perspective, including other buffers, diluents, filters, needles and syringes. In addition, the article contains a package insert with instructions for use, including, for example, instructions to the user of the composition to administer the plasminogen composition and other medications to treat the accompanying disease to the patient.

EXAMPLE

Figure 1:
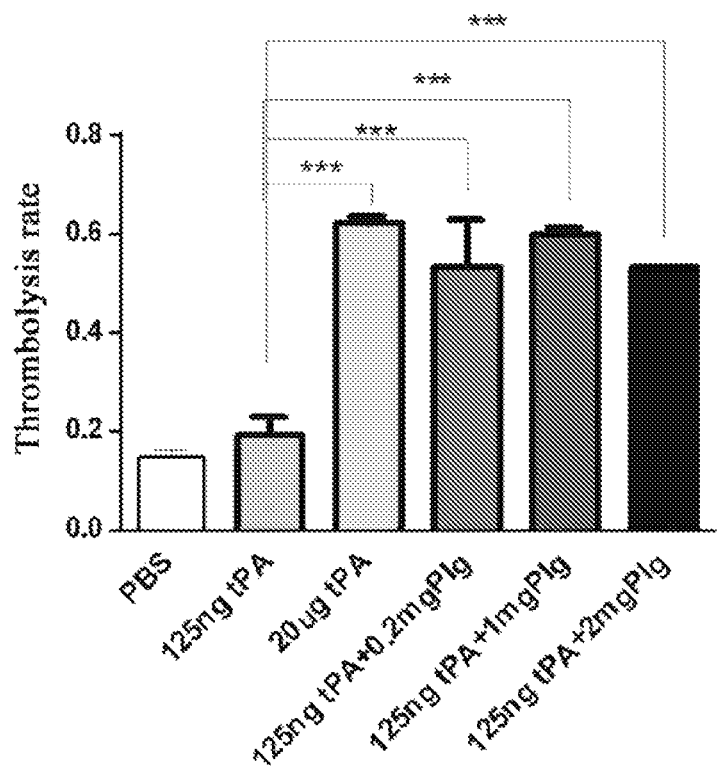
FIG. 1 shows the thrombolytic effect of different doses of plasminogen on 20-hour old thrombus in the presence of 125 ng tPA, incubation at 37° C. for 1 hour.

Materials and Methods:
In Vivo Experiments:

Experimental Animals

C57 mice (6-8 weeks old) are purchased from Experimental Animal Center of Southern Medical University. Purchased mice are kept in barrier environment animal rooms. Db/db mice are purchased from Nanjing Institute of Biomedical Research.

Experimental Design and Administration

After the dissection of carotid arteries from all the animals in the control group and the experimental group, unilateral carotid artery thrombosis is modeled with a filter paper containing 10% $FeCl_3$ for 5 minutes. Intravenous injection of plasminogen is started within 1 hour after the model is established, and the control group is intravenously injected with an equal volume of PBS. After 3 hours, the corresponding jugular vein thrombi and the muscles near the contralateral vein are removed. The thrombi and the muscles near the contralateral vein are homogenized using a grinder, and the supernatant is removed after centrifugation. The supernatant is assayed for its total protein by BCA method, and the plasminogen content in the homogenate is measured by enzyme-linked immunosorbent assay, to calculate the plasminogen content in the certain amount of total protein. Study the specificity of thrombolysis in vivo by plasminogen.

In addition, 24-25-week-old db/db mice are administered solvent PBS or plasminogen through tail veins respectively, as control and experimental animals. After 31 days, eyeballs are taken for D-dimer detection and immunohistochemical staining of fibrin is performed on nerve, liver, kidney and heart, to study the thrombolytic effect of plasminogen in vivo.

Blood D-Dimer Analysis

Eyeballs are taken from the mice to draw blood and obtain plasma. Experiments are performed according to the D-dimer kit (Wuhan USCN, China). After the test is completed, a reading is performed at 450 nm using a microplate reader (Biotek, USA) for data analysis.

Immunohistochemical Analysis

Nerve, liver, kidney and heart are collected, and fixed in 10% neutral formalin for more than 24 hours. The fixed tissues are dehydrated by gradient ethanol and embedded in paraffin. The paraffin is sectioned to a thickness of 5 μm and the sections are washed once after deparaffinization to water. Then circle the tissues with a PAP pen. Incubate with hydrogen peroxide diluted with 0.3% methanol for 15 minutes and wash three times. Block with 10% normal serum homologous to the secondary antibody for 10 minutes and absorb excess serum. Incubate with primary antibody for 30 minutes at room temperature or overnight at 4☐ and wash three times with TBS. Incubate with HRP-labeled secondary antibody for 30 minutes at room temperature and wash three times with TBS. Stain according to DAB kit (vector laboratories, Inc., USA), counterstain with hematoxylin for 30 seconds, flush with water for 5 minutes and then wash once with TBS. Gradient dehydration, clearing and mounting are followed. The antibodies used are: the marker antibody is anti-Fibrinogen antibody (Abcam). Sections are observed under an optical microscope (Olympus, BX43).

In Vitro Thrombolytic Experimental Design:

Healthy human plasma is collected in an ELISA 96-well plate. Add a fixed amount of thrombin (Sigma, USA) to form a thrombus, and then perform the following different experiments. Add fixed amounts of tPA, uPA (sigma, USA) and different amounts of plasminogen, fixed amounts of plasminogen and different amounts of tPA, uPA, streptokinase (sigma, USA), and add PBS in the control group. Incubate for different lengths of time until thrombolysis occurs. The absorbance readings and the time of each measurement are observed and recorded on a microplate reader (Biotek, USA) at the wavelength of OD405. The data is analyzed.

Example 1 Thrombolytic Effect of Different Doses of Plasminogen on 20-Hour Old Thrombus when Incubated at 37° C. for 1 Hour at 125 ng tPA Whole blood of two SD rats is individually collected into Eppendorf (EP) tubes and the supernatant is discarded after incubation at 37° C. for 20 h to form old thrombus[33, 34]. Add PBS and wash repeatedly for 5-10 times until the added PBS solution becomes clear. Dry the thrombus with absorbent paper as much as possible. Then place the thrombus evenly in each EP tube and weigh the thrombus. Try to make the weight of each thrombus consistent. The thrombi are divided into PBS blank control group, 125 ng tPA control group, 20 μg tPA control group, 0.2 mg plasminogen group, 1 mg plasminogen group and 2 mg plasminogen group. 3 tubes per group. 1 mL PBS is added in PBS blank control group; 1 mL PBS and 125 ng tPA are added in 125 ng tPA control group; 1 mL PBS and 20 μg tPA are added in 20 μg tPA control group; 1 mL PBS, 125 ng tPA and 0.2 mg plasminogen are added in 0.2 mg plasminogen group; 1 mL PBS, 125 ng tPA and 1 mg plasminogen are added in 1 mg plasminogen group; 1 mL PBS, 125 ng tPA and 2 mg plasminogen are added in 2 mg plasminogen group. All reactions are performed in an incubator at 37□. After incubation for 1 hour, the supernatant is aspirated. Dry the thrombus with absorbent paper as much as possible and weigh the thrombus. Calculate the thrombolysis rate.

According to the literature, the content of tPA is 5-10 ng/mL under normal physiological conditions[35], while in the case of strenuous exercise or venous congestion, the content of tPA in the body increases from 20 times to 100 times, that is, over 100 ng/mL[36]. Therefore, the dose of tPA used in this experiment is 125 ng/mL to mimic the naturally occurring tPA content in the case of in vivo thrombosis.

The results show that for old thrombi formed in vitro for 20 hours, the thrombolysis rates when adding 0.2 mg, 1 mg, 2 mg of plasminogen under the condition of 125 ng tPA are significantly higher than those when adding 125 ng of tPA alone and the statistical differences are extremely significant, indicating that in the case of naturally occurring tPA levels in the presence of thrombosis in the body, the addition of 0.2 mg or more of plasminogen for 1 hour can significantly promote thrombolysis. Under the condition of 125 ng tPA, adding 1 mg plasminogen can achieve the same thrombolytic effect of in vivo injection of 20 μg tPA (according to instructions for alteplase for injection produced by Boehringer Ingelheim, the dose required for thrombolysis in the case of thrombosis in vivo is converted into the required injection dose in rats). That is to achieve the same thrombolysis rate, if there is 1 mg plasminogen in vivo, the required tPA amount can be reduced to the original 1/160. In addition, under the condition of 125 ng tPA, the addition of plasminogen 1 mg reaches the peak of plasminogen thrombolysis, and the addition of 1 times more plasminogen has a decreasing trend in the thrombolysis rate, indicating there is saturation for the addition of plasminogen and the saturation is about 1 to 2 mg (FIG. 1).

Example 2 Thrombolytic Effect of Different Doses of Plasminogen on 20-Hour Old Thrombus when Incubated at 37° C. for 2 Hours at 125 ng tPA Whole blood of two SD rats is individually collected into EP tubes and the supernatant is discarded after incubation at 37° C. for 20 h to form old thrombus[33, 34]. Add PBS and wash repeatedly for 5-10 times until the added PBS solution becomes clear. Dry the thrombus with absorbent paper as much as possible. Then place the thrombus evenly in each EP tube and weigh the thrombus. Try to make the weight of each thrombus consistent. The thrombi are divided into PBS blank control group, 125 ng tPA control group, 20 μg tPA control group, 0.2 mg plasminogen group, 1 mg plasminogen group and 2 mg plasminogen group. 3 tubes per group. 1 mL PBS is added in PBS blank control group; 1 mL PBS and 125 ng tPA are added in 125 ng tPA control group; 1 mL PBS and 20 μg tPA are added in 20 μg tPA control group; 1 mL PBS, 125 ng tPA and 0.2 mg plasminogen are added in 0.2 mg plasminogen group; 1 mL PBS, 125 ng tPA and 1 mg plasminogen are added in 1 mg plasminogen group; 1 mL PBS, 125 ng tPA and 2 mg plasminogen are added in 2 mg plasminogen group. All reactions are performed in an incubator at 37□. After incubation for 2 hours, the supernatant is aspirated. Dry the thrombus with absorbent paper as much as possible and weigh the thrombus. Calculate the thrombolysis rate.

According to the literature, the content of tPA is 5-10 ng/mL under normal physiological conditions[35], while in the case of strenuous exercise or venous congestion, the content of tPA in the body increases from 20 times to 100 times, that is, over 100 ng/mL[36]. Therefore, the dose of tPA used in this experiment is 125 ng/mL to mimic the naturally occurring tPA content in the case of in vivo thrombosis.

Figure 2:
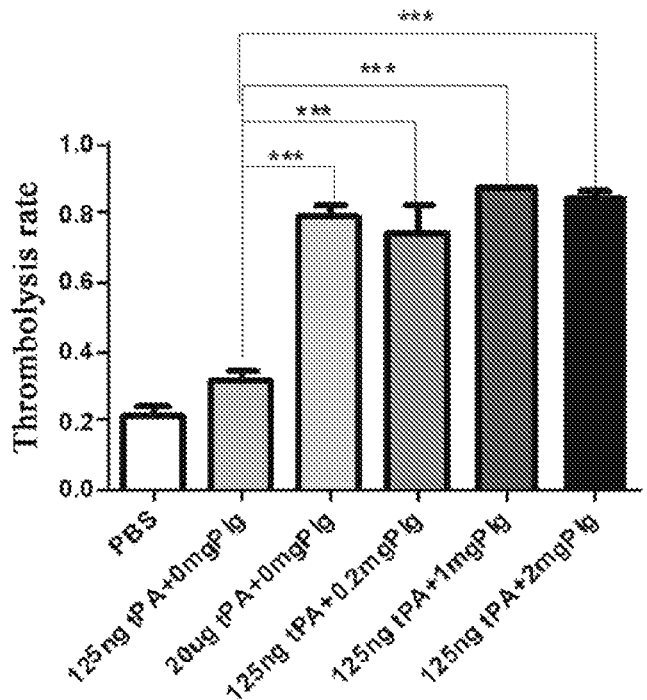
FIG. 2 shows the thrombolytic effect of different doses of plasminogen on 20-hour old thrombus in the presence of 125 ng tPA, incubation at 37° C. for 2 hours.

The results show that for old thrombi formed in vitro for 20 hours, compared with Example 1, the thrombolysis rate increases as the reaction time prolonged in each group. The thrombolysis rates when adding 0.2 mg, 1 mg, 2 mg of plasminogen under the condition of 125 ng tPA are significantly higher than those when adding 125 ng of tPA alone and the statistical differences are extremely significant, indicating that in the case of naturally occurring tPA doses in the presence of thrombosis in the body, the addition of 0.2 mg or more of plasminogen for 2 hours can significantly promote thrombolysis. After 2 hours of reaction, the thrombolytic effects of the 1 mg and 2 mg plasminogen group are superior to the normal injection dose in vivo of 20 μg tPA control group (according to instructions for alteplase for injection produced by Boehringer Ingelheim, the dose required for thrombolysis in the case of thrombosis in vivo is converted into the required injection dose in rats). That is to achieve the same thrombolysis rate, if there is 1 mg of plasminogen in the system, the required tPA amount can be reduced to less than 1/160 of the amount of tPA required (20 μg) without 1 mg of plasminogen in the system (FIG. 2).

Example 3 Thrombolysis Rate on 20-Hour Old Thrombus at 10 ng tPA Increases with Increasing Plasminogen Dose Whole blood of two SD rats is individually collected into EP tubes and the supernatant is discarded after incubation at 37° C. for 20 h to form old thrombus[33, 34]. Add PBS and wash repeatedly for 5-10 times until the added PBS solution becomes clear. Dry the thrombus with absorbent paper as much as possible. Then place the thrombus evenly in each EP tube and weigh the thrombus. Try to make the weight of each thrombus consistent. The thrombi are divided into PBS blank control group, 10 ng tPA control group, 0.2 mg plasminogen control group, 0.2 mg plasminogen group, 1 mg plasminogen group and 2 mg plasminogen group. 3 tubes per group. 1 mL PBS is added in PBS blank control group; 1 mL PBS and 10 ng tPA are added in 10 ng tPA control group; 1 mL PBS and 0.2 mg plasminogen are added in 0.2 mg plasminogen control group; 1 mL PBS, 10 ng tPA and 0.2 mg plasminogen are added in 0.2 mg plasminogen group; 1 mL PBS, 10 ng tPA and 1 mg plasminogen are added in 1 mg plasminogen group; 1 mL PBS, 10 ng tPA and 2 mg plasminogen are added in 2 mg plasminogen group. All reactions are performed in an incubator at 37□. After incubation for 2 hours, the supernatant is aspirated. Dry the thrombus with absorbent paper as much as possible and weigh the thrombus. Calculate the thrombolysis rate.

According to the literature, the content of tPA is 5-10 ng/mL under normal physiological conditions[35]. Therefore, the dose of tPA used in this experiment is 10 ng/mL to mimic the naturally occurring tPA content in normal physiological conditions in vivo.

Figure 3:
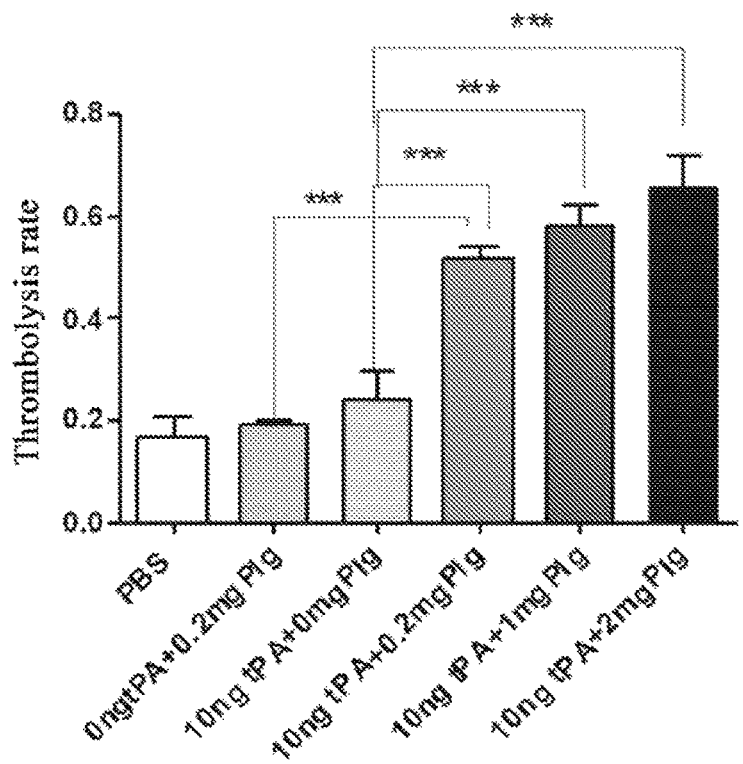
FIG. 3 shows the thrombolytic effect of different doses of plasminogen on 20-hour old thrombus when incubated at 37° C. for 2 hours at 10 ng tPA.

The results show that for old thrombi formed in vitro for 20 hours, the thrombolysis rate of each groups added with plasminogen is higher than that of the control group in which the physiological dose of tPA alone is added, under the condition of naturally occurring tPA content (10 ng) under normal physiological conditions in the body and the statistical differences are extremely significant. Moreover, with the increase of the amount of plasminogen additive, the corresponding thrombolysis rate also shows a gradient increase trend, indicating that the rate of dissolution of 20-hour old thrombus can be adjusted by adjusting the dose of plasminogen. In addition, in the presence of 0.2 mg plasminogen, the thrombolysis efficiency is significantly higher in the group with the in vivo physiological level of tPA (10 ng) than in the group without the addition of tPA, and the thrombolytic effect of adding 0.2 mg plasminogen alone is similar to that of adding control PBS, indicating that physiological levels of tPA play a key role in thrombolysis by plasminogen (FIG. 3).

Example 4 Thrombolysis Rate on 72-Hour Old Thrombus at 125 ng tPA Increases with Increasing Plasminogen Dose Whole blood of two SD rats is individually collected into EP tubes and the supernatant is discarded after incubation at 37° C. for 72 hours to form old thrombus[36]. Add PBS and wash repeatedly for 5-10 times until the added PBS solution becomes clear. Dry the thrombus with absorbent paper as much as possible. Then place the thrombus evenly in each EP tube and weigh the thrombus. Try to make the weight of each thrombus consistent. The thrombi are divided into PBS blank control group, 125 ng tPA control group, 0.2 mg plasminogen control group, 0.2 mg plasminogen group, 1 mg plasminogen group and 2 mg plasminogen group. 3 tubes per group. 1 mL PBS is added in PBS blank control group; 1 mL PBS and 125 ng tPA are added in 125 ng tPA control group; 1 mL PBS and 0.2 mg plasminogen are added in 0.2 mg plasminogen control group; 1 mL PBS, 125 ng tPA and 0.2 mg plasminogen are added in 0.2 mg plasminogen group; 1 mL PBS, 125 ng tPA and 1 mg plasminogen are added in 1 mg plasminogen group; 1 mL PBS, 125 ng tPA and 2 mg plasminogen are added in 2 mg plasminogen group. All reactions are performed in an incubator at 37□. After incubation for 2 hours, the supernatant is aspirated. Dry the thrombus with absorbent paper as much as possible and weigh the thrombus. Calculate the thrombolysis rate.

According to the literature, the content of tPA is 5-10 ng/mL under normal physiological conditions[35], while in the case of strenuous exercise or venous congestion, the content of tPA in the body increases from 20 times to 100 times, that is, over 100 ng/mL[36]. Therefore, the dose of tPA used in this experiment is 125 ng/mL to mimic the naturally occurring tPA content in the case of in vivo thrombosis.

Figure 4:
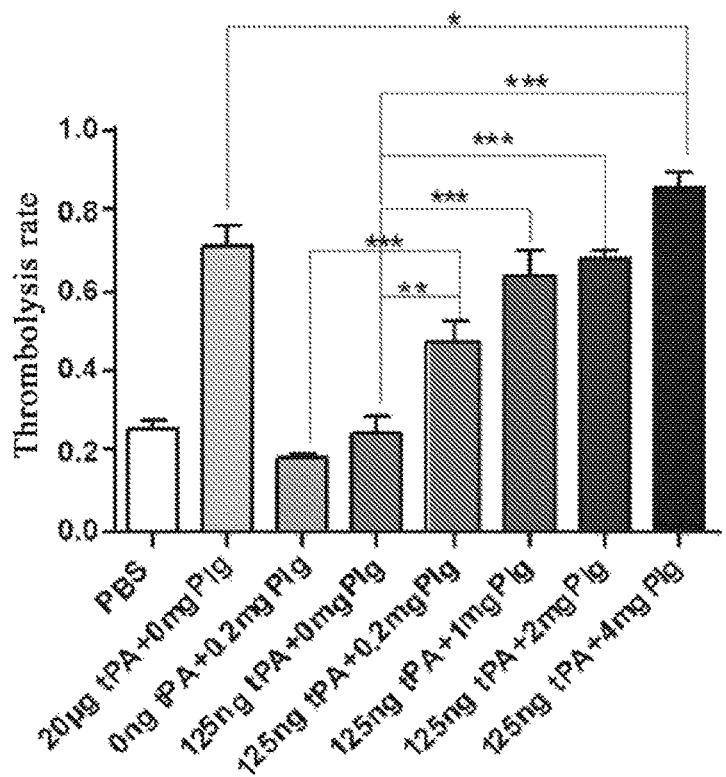
FIG. 4 shows the thrombolytic effect of different doses of plasminogen on 72-hour old thrombus when incubated at 37° C. for 2 hours at 125 ng tPA.

The results show that for old thrombi formed in vitro for 72 hours, the thrombolysis rates with addition of plasminogen under the condition of 125 ng tPA are higher than those when adding 125 ng of tPA alone and the statistical differences are extremely significant, indicating that in the case of naturally occurring tPA dose (125 ng) in the presence of thrombosis in the body, the addition of 0.2 mg or more of plasminogen for 2 hours can significantly promote thrombolysis on 72-hour old thrombus. Moreover, with the gradient increase of the dose of plasminogen additive, its thrombolysis rate also shows a gradient increase trend, indicating that the rate of dissolution of old thrombus can be adjusted by adjusting the dose of plasminogen. In addition, the thrombolysis rate of adding 4 mg of plasminogen exceeds the thrombolysis rate of 20 μg tPA of normal injection dose (according to instructions for alteplase for injection produced by Boehringer Ingelheim, the dose required for thrombolysis in the case of thrombosis in vivo is converted into the required injection dose in rats) in vivo in this experiment, indicating that under the condition of naturally occurring tPA dose (125 ng) in the presence of thrombosis in the body, the effect of adding plasminogen alone to dissolve old thrombus is superior to that of existing thrombolytic drugs (FIG. 4), which shows that plasminogen can be a thrombolytic material with better thrombolytic effect.

In addition, in Example 2, the addition of 125 ng of tPA alone significantly increases the ability to dissolve the 20-hour thrombus compared to the control PBS group. However, in the present example, for the 72-hour old thrombus, similar to the in vivo situation, the thrombolytic effect is almost the same for the group adding 125 ng tPA alone and the control PBS group, indicating that as the thrombus is getting older, the thrombolytic capacity of tPA naturally produced under physiological conditions gradually decreases, which in one aspect indicates that the model used in the examples can mimic the situation in vivo to some extent.

Example 5 Thrombolysis Rate on 72-Hour Old Thrombus at 10 ng tPA Increases with Increasing Plasminogen Dose Whole blood of two SD rats is individually collected into EP tubes and the supernatant is discarded after incubation at 37° C. for 72 h to form old thrombus[36]. Add PBS and wash repeatedly for 5-10 times until the added PBS solution becomes clear. Dry the thrombus with absorbent paper as much as possible. Then place the thrombus evenly in each EP tube and weigh the thrombus. Try to make the weight of each thrombus consistent. The thrombi are divided into PBS blank control group, 10 ng tPA control group, 20 μg tPA control group, 0.2 mg plasminogen control group, 0.2 mg plasminogen group, 1 mg plasminogen group, 2 mg plasminogen group and 4 mg plasminogen group. 3 tubes per group. 1 mL PBS is added in PBS blank control group; 1 mL PBS and 10 ng tPA are added in 10 ng tPA control group; 1 mL PBS and 20 μg tPA are added in 20 μg tPA control group; 1 mL PBS and 0.2 mg plasminogen are added in 0.2 mg plasminogen control group; 1 mL PBS, 10 ng tPA and 0.2 mg plasminogen are added in 0.2 mg plasminogen group; 1 mL PBS, 10 ng tPA and 1 mg plasminogen are added in 1 mg plasminogen group; 1 mL PBS, 10 ng tPA and 2 mg plasminogen are added in 2 mg plasminogen group; 1 mL PBS, 10 ng tPA and 4 mg plasminogen are added in 4 mg plasminogen group. All reactions are performed in an incubator at 37□. After incubation for 2 hours, the supernatant is aspirated. Dry the thrombus with absorbent paper as much as possible and weigh the thrombus. Calculate the thrombolysis rate.

According to the literature, the content of tPA is 5-10 ng/mL under normal physiological conditions[35]. Therefore, the dose of tPA used in this experiment is 10 ng/mL to mimic the naturally occurring tPA content in normal physiological conditions in vivo.

Figure 5:
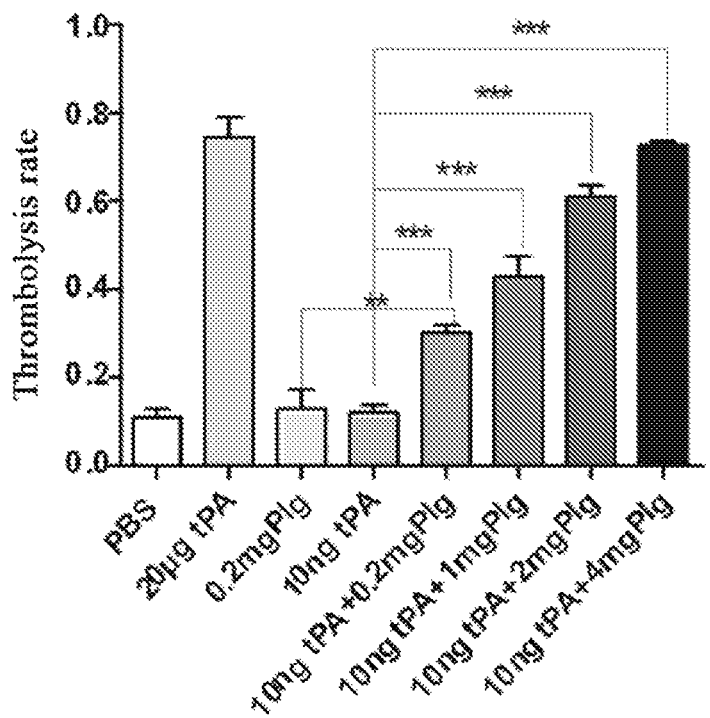
FIG. 5 shows the thrombolytic effect of different doses of plasminogen on 72-hour old thrombus when incubated at 37° C. for 2 hours at 10 ng tPA.
Figure 6:
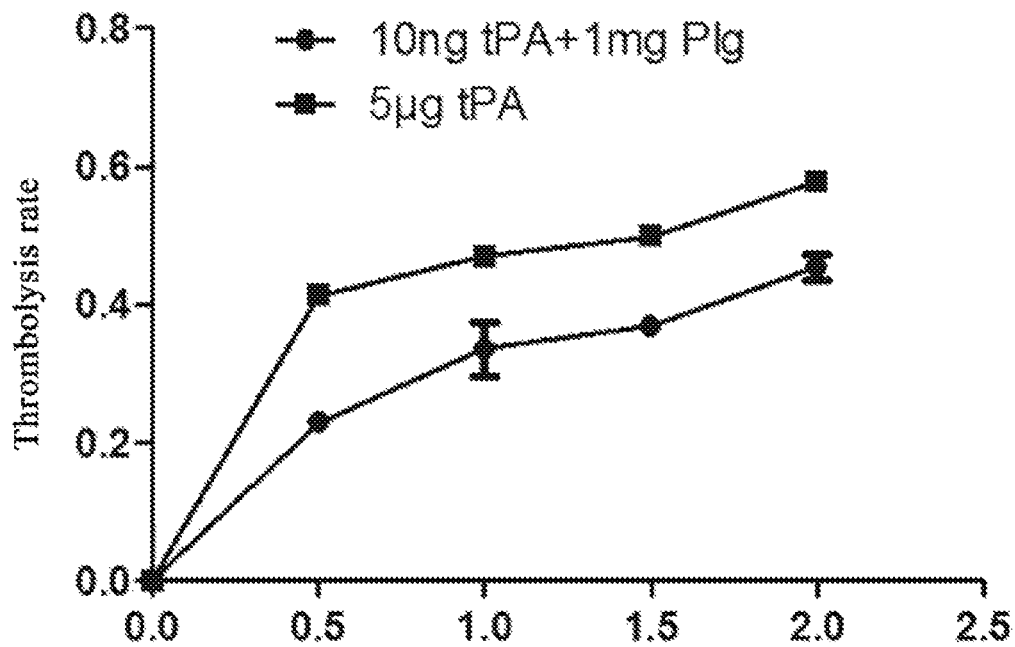
FIG. 6 shows changes in thrombolysis rates over time with the addition of 10 ng of tPA and 1 mg of plg or 5 μg of tPA alone to 20-hour old thrombus.

The experimental result shows that for old thrombi formed in vitro for 72 hours, the thrombolysis rate of adding plasminogen is higher than that of adding 10 ng tPA alone when the normal physiologic tPA content is 10 ng/mL in the body and the difference is extremely significant. It is demonstrated that under the condition of naturally occurring tPA dose (10 ng) in the presence of thrombosis in the body, the addition of 0.2 mg or more of plasminogen for 2 hours can significantly promote the dissolution of 72-hour old thrombus. As the dose of plasminogen added increases, the thrombolysis rate also shows a gradient increase, indicating that the rate of dissolving old thrombus can be adjusted by adjusting the dose of plasminogen. Furthermore, the thrombolysis rate of the group with 4 mg of plasminogen added is similar to that of the normal tPA injection dose (according to instructions for alteplase for injection produced by Boehringer Ingelheim, the dose required for thrombolysis in the case of thrombosis in vivo is converted into the required injection dose in rats) (FIG. 5), indicating that under the Experiments show that for a 20-hour old thrombus, the total thrombolysis rate increases in both groups over time, but between 0 and 0.5 hours and 0.5 to 1 hour, the thrombolytic curve slope of plasminogen group is lower than that of tPA group (FIG. 6). Table 1 shows the comparison of the thrombolytic efficiency of 1 mg of plasminogen and the thrombolytic efficiency of 5 μg of tPA alone over time in the presence of 10 ng of tPA. As shown in Table 1, 75% of the total thrombolysis rate for 2 hours in the plasminogen group is concentrated within about 1 hour, and 75% of the total thrombolysis rate for 2 hours in the tPA control group is concentrated in about 0.5 hours. These data clearly show that, relative to tPA, the thrombolysis rate of plasminogen is more moderate than that of tPA (FIG. 6, Table 1).

TABLE 1

Changes of the thrombolytic efficiency of 1 mg plasminogen and the thrombolytic efficiency of 5 μg tPA alone over time in the presence of 10 ng tPA

| | Total thrombolysis rate after incubation for 0.5 hours | Total thrombolysis rate after incubation for 1 hour | Total thrombolysis rate after incubation for 1.5 hours | Total thrombolysis rate after incubation for 2 hours | 50% of the total thrombolysis rate for 2 hours | 75% of the total thrombolysis rate for 2 hours |
|---|---|---|---|---|---|---|
| 10 ng tPA + 1 mg Plg Group | 22.80% | 33.55% | 36.91% | 45.42% | 22.71% | 34.07% |
| 5 μg tPA Group | 41.28% | 46.88% | 49.88% | 57.77% | 28.88% | 43.33% | condition of physiological level of tPA dose (10 ng), the effect of adding plasminogen alone to dissolve old thrombus can reach the effect of existing thrombolytic drugs. In this sense, plasminogen is expected to become a new thrombolytic drug for old thrombus.

Example 6 Plasminogen Moderately Dissolves 20-Hour Old Thrombus

Whole blood of two SD rats is individually collected into EP tubes and the supernatant is discarded after incubation at 37° C. for 20 hours to form old thrombus[33, 34]. Add PBS and wash repeatedly for 5-10 times until the added PBS solution becomes clear. Dry the thrombus with absorbent paper as much as possible. Then place the thrombus evenly in each EP tube and weigh the thrombus. Try to make the weight of each thrombus consistent. The thrombi are divided into two groups and 12 samples per group. The first group is tPA control group, in which 1 mL PBS and 5 μg tPA are added; the second group is plasminogen group, in which 1 mL PBS, 10 ng tPA and 1 mg plasminogen are added. Pre-experiments prove that the thrombolysis rates of these two groups for 20-hour old thrombi are similar within 2 hours (data not shown). All reactions are performed in an incubator at 37□. Samples are collected at 0.5 h, 1 h, 1.5 h and 2 h respectively and three samples are collected from the two groups respectively at each time point. Aspirate the supernatant. Dry the thrombus with absorbent paper as much as possible and weigh the thrombus. Calculate the thrombolysis rate.

According to the literature, the content of tPA is 5-10 ng/mL under normal physiological conditions[35]. Therefore, the dose of tPA used in this experiment is 10 ng/mL to mimic the naturally occurring tPA content in normal physiological conditions in vivo.

Example 7 Plasminogen Promotes the Dissolution of 20-Hour Old Thrombus Under the Condition of 100 ng uPA Whole blood of two SD rats is individually collected into EP tubes and the supernatant is discarded after incubation at 37° C. for 20 hours to form old thrombus[33, 34]. Add PBS and wash repeatedly for 5-10 times until the added PBS solution becomes clear. Dry the thrombus with absorbent paper as much as possible. Then place the thrombus evenly in each EP tube and weigh the thrombus. Try to make the weight of each thrombus consistent. The thrombi are divided into PBS blank control group, 100 ng uPA control group, 0.2 mg plasminogen control group, 0.2 mg plasminogen group, 1 mg plasminogen group and 2 mg plasminogen group. 3 tubes per group. 1 mL PBS is added at the beginning in PBS blank control group; 1 mL PBS and 100 ng uPA are added in 100 ng uPA control group; 1 mL PBS and 0.2 mg plasminogen are added in 0.2 mg plasminogen control group; 1 mL PBS, 100 ng uPA and 0.2 mg plasminogen are added in 0.2 mg plasminogen group; 1 mL PBS, 100 ng uPA and 1 mg plasminogen are added in 1 mg plasminogen group; 1 mL PBS, 100 ng uPA and 2 mg plasminogen are added in 2 mg plasminogen group. All reactions are performed in an incubator at 37□. After incubation for 1 hour, the supernatant is aspirated. Dry the thrombus with absorbent paper as much as possible and weigh the thrombus. Calculate the thrombolysis rate.

According to the literature, the tPA Michaelis constant is $0.18 \times 10^{-7}$ mol/L during the enzymatic reaction with plasminogen as substrate[37], while the Michaelis constant of uPA is $2.43 \times 10^{-7}$ mol/L[38]. In other words, under the same reaction conditions, the affinity of tPA is about 10 times that of uPA within the same reaction time. Therefore, in this experiment, the dose of uPA is estimated to be 100 ng/ml according to the 10 ng tPA/ml used in Example 3.

The results show that for old thrombi formed in vitro for 20 hours, after changing the plasminogen activator 10 ng tPA to 100 ng uPA, the thrombolysis rates of the groups adding 0.2 mg, 1 mg, 2 mg of plasminogen are significantly higher than those when adding 100 ng of uPA alone and the statistical differences are extremely significant (P<0.01; *P<0.001).

Figure 7:
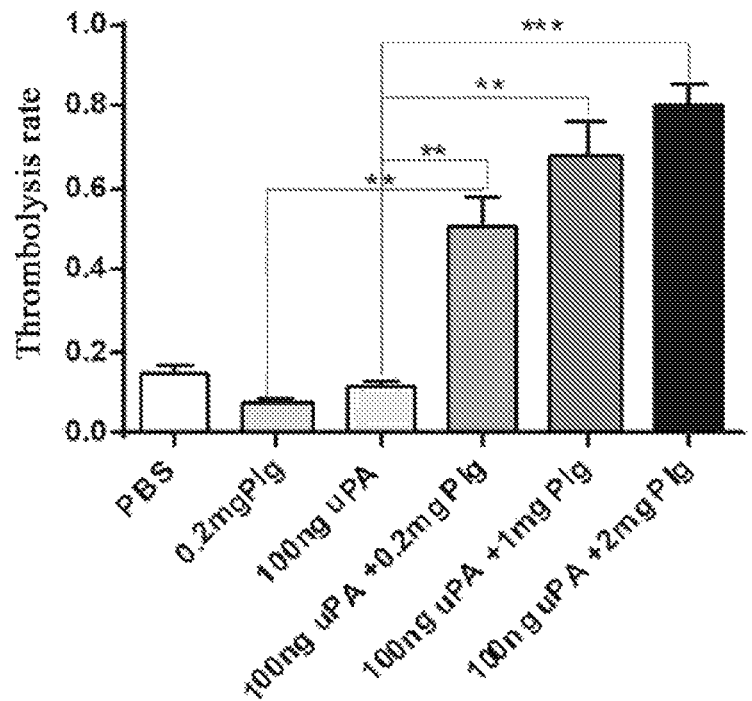
FIG. 7 shows the thrombolytic effect of different doses of plasminogen on 20-hour old thrombus when incubated at 37° C. for 1 hour at 100 ng uPA.

It is demonstrated that in the case of 100 ng of uPA dose, the addition of 0.2 mg or more of plasminogen for 1 hour can significantly promote thrombolysis and with the increase of the plasminogen additive gradient, the thrombolysis rate also increases significantly (FIG. 7). It indicates that under the condition of 100 ng uPA, plasminogen can promote the dissolution of old thrombus.

Example 8 Plasminogen Promotes the Dissolution of 20-Hour Old Thrombus Under the Condition of 1 ng uPA Whole blood of two SD rats is individually collected into EP tubes and the supernatant is discarded after incubation at 37° C. for 20 hours to form old thrombus[33, 34]. Add PBS and wash repeatedly for 5-10 times until the added PBS solution becomes clear. Dry the thrombus with absorbent paper as much as possible. Then place the thrombus evenly in each EP tube and weigh the thrombus. Try to make the weight of each thrombus consistent. The thrombi are divided into PBS blank control group, 1 ng uPA control group, 0.2 mg plasminogen control group, 0.2 mg plasminogen group, 1 mg plasminogen group and 2 mg plasminogen group. 3 tubes per group. 1 mL PBS is added in PBS blank control group; 1 mL PBS and 1 ng uPA are added in 1 ng uPA control group; 1 mL PBS and 0.2 mg plasminogen are added in 0.2 mg plasminogen control group; 1 mL PBS, 1 ng uPA and 0.2 mg plasminogen are added in 0.2 mg plasminogen group; 1 mL PBS, 1 ng uPA and 1 mg plasminogen are added in 1 mg plasminogen group; 1 mL PBS, 1 ng uPA and 2 mg plasminogen are added in 2 mg plasminogen group. All reactions are performed in an incubator at 37□. After incubation for 2 hours, the supernatant is aspirated. Dry the thrombus with absorbent paper as much as possible and weigh the thrombus. Calculate the thrombolysis rate.

Figure 8:
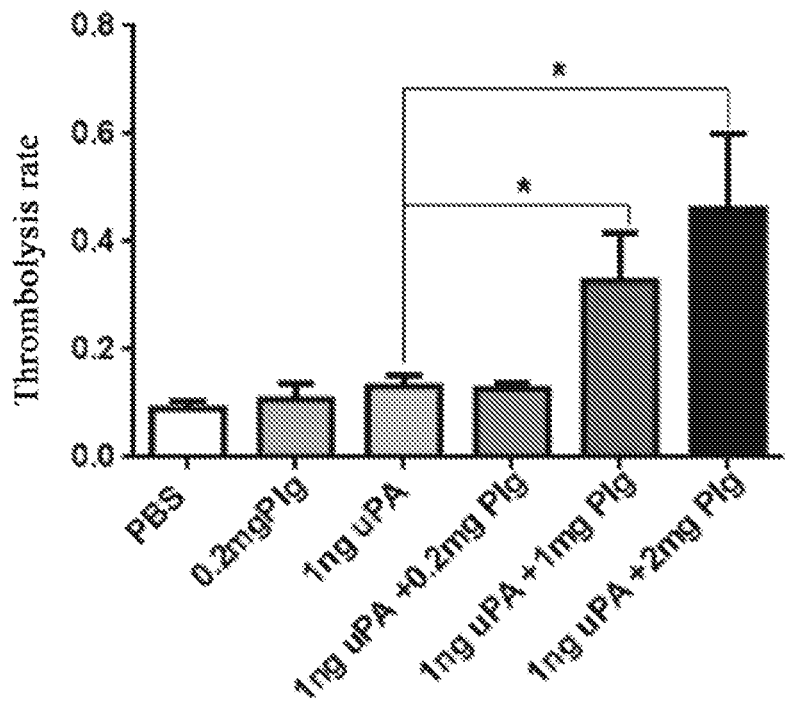
FIG. 8 shows the thrombolytic effect of different doses of plasminogen on 20-hour old thrombus when incubated at 37° C. for 2 hours at 1 ng uPA.

According to the literature, the content of uPA is 1 ng/mL under normal physiological conditions[35]. Therefore, the dose of uPA used in this experiment is 1 ng/mL to mimic the naturally occurring uPA content in normal physiological conditions in vivo. The results show that for old thrombi formed in vitro for 20 hours, when the usage of uPA is reduced to 1 ng of normal body content, the thrombolysis rate of old thrombus is generally slow. However, the thrombolysis rates in the 1 mg and 2 mg plasminogen groups are significantly higher than those in the 1 ng uPA control group, with statistical differences. It indicates that under the condition of 1 ng uPA, the addition of plasminogen significantly promotes the dissolution of old thrombus (FIG. 8).

Example 9 Rebleeding Experiment after Intravenous Injection of tPA and Plasminogen in Mice Fifty-five 11-week-old C57 wild-type male mice are selected and general anesthesia is performed with 3% pentobarbital. Cut 3 mm of tails respectively, place tails in 37□ warm water and observe the condition of tail bleeding[39]. After hemostasis, the mice are randomly divided into two groups, 5 in the tPA group and 50 in the plasminogen group. In the tPA group, 400 μg/0.05 mL/body of tPA is injected through the orbital vein; in the plasminogen group, 1 mg/0.05 mL/body of plasminogen is injected through the orbital vein. During the experiment, the mouse tail vein is always placed in warm water at 37° C. The condition of experimental bleeding is observed for 20 minutes and recorded.

The experimental results show that intravenous injection of 400 μg tPA can cause rebleeding in tail wounds of wounded mice that have already been coagulated, which is a common side effect of tPA drugs. However, mice injected intravenously with 1 mg of plasminogen do not have such side effects (Table 2), suggesting that plasminogen is safer than tPA.

TABLE 2

In vivo hemorrhage experimental results after intravenous injection of tPA or plasminogen in mice

| Drugs injected | Rebleeding condition (20 minutes after injection) | | Total number of mice |
|---|---|---|---|
| | Yes | No | |
| tPA 400 μg | 2 | 3 | 5 |
| Plg 1 mg | 0 | 50 | 50 |

Example 10 Specific Adsorption Experiment of Plasminogen on Thrombus In Vivo

Nine wild-type mice are selected and are randomly divided into three groups, solvent PBS control group, 0.2 mg plasminogen group and 1 mg plasminogen group. 3 mice per group. General anesthesia is performed by using 3% pentobarbital and the jugular veins of the mice are isolated. Venous thrombus is formed by applying absorbent paper (3 mm×5 mm) impregnated with 10% $FeCl_3$ solution to the jugular vein for 5 minutes. Immediately after thrombus formation, plasminogen or solvent PBS is administered. In solvent PBS control group, 100 μl PBS is injected through tail vein and in 1 mg plasminogen group and 0.2 mg plasminogen group, 1 mg and 0.2 mg plasminogen are administered by tail vein injection, respectively. After 3 hours, the corresponding jugular vein thrombi and the muscles near the contralateral vein are removed. The thrombi and the muscles near the contralateral vein are homogenized using a grinder, and the supernatant is removed after centrifugation. The supernatant is assayed for its total protein by BCA method, and the plasminogen content in the homogenate is measured by enzyme-linked immunosorbent assay, to calculate the plasminogen content in the certain amount of total protein.

Figure 9:
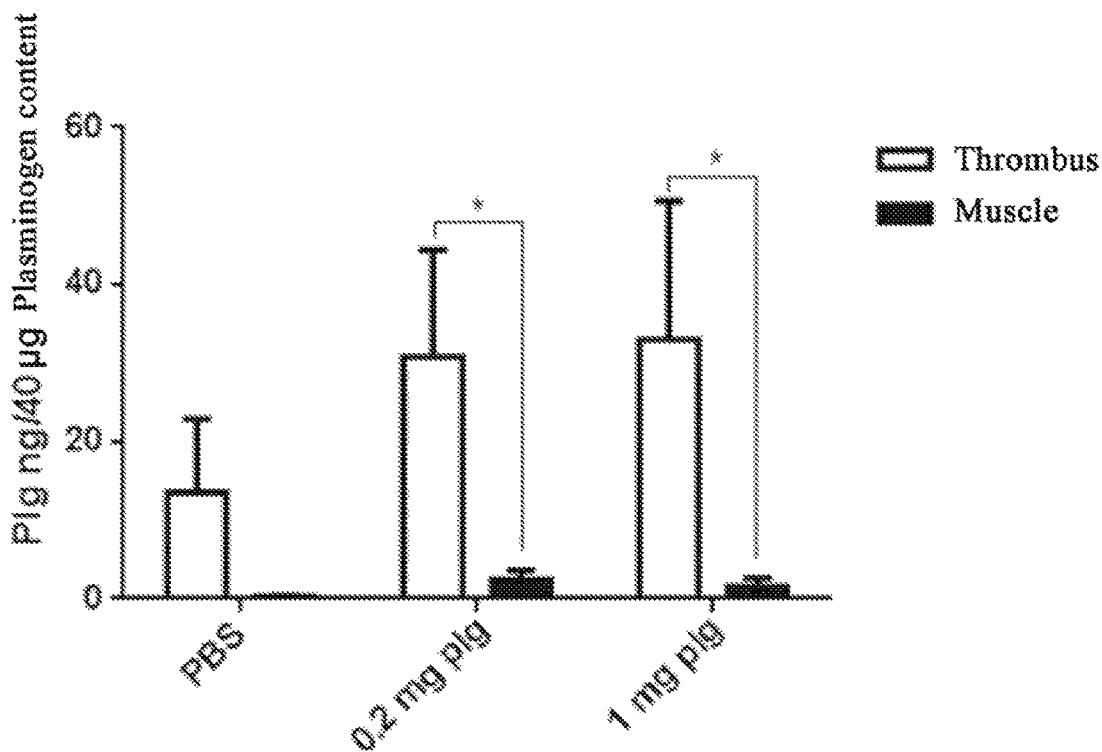
FIG. 9 shows the results of a specific adsorption experiment of plasminogen for thrombus in vivo.

The results show that the content of plasminogen in thrombus after thrombus formation is significantly higher than that in muscle. In addition, the plasminogen content in the thrombus is further increased after intravenous injection of plasminogen. These results indicate that in the presence of in vivo thrombi plasminogen can specifically bind to thrombi (FIG. 9) and further exerts thrombolytic effects, whereas once tPA is injected into blood vessels, it will non-specifically catalyze thrombolysis in blood vessels. The results of this experiment indicate that plasminogen has a significant advantage of specific thrombolysis over tPA.

Example 11 Thrombolysis Rate of 30-Minute Fresh Thrombus after Adding Plasminogen is Significantly Increased Whole blood of two SD rats is individually collected into EP tubes and the supernatant is discarded after incubation at 37° C. for 30 minutes to form fresh thrombus[33]. Add PBS and wash repeatedly for 5-10 times until the added PBS solution becomes clear. Dry the thrombus with absorbent paper as much as possible. Then place the thrombus evenly in each EP tube and weigh the thrombus. Try to make the weight of each thrombus consistent. The thrombi are divided into PBS blank control group, 125 ng tPA control group, 0.2 mg plasminogen group, 1 mg plasminogen group and 2 mg plasminogen group. 2 tubes per group. 1 mL PBS is added in PBS blank control group; 1 mL PBS and 125 ng tPA are added in tPA control group; 1 mL PBS, 125 ng tPA and 0.2 mg plasminogen are added in 0.2 mg plasminogen group; 1 mL PBS, 125 ng tPA and 1 mg plasminogen are added in 1 mg plasminogen group; 1 mL PBS, 125 ng tPA and 2 mg plasminogen are added in 2 mg plasminogen group. All reactions are performed in an incubator at 37□. After incubation for 2 hours, the supernatant is aspirated. Dry the thrombus with absorbent paper as much as possible and weigh the thrombus. Calculate the thrombolysis rate.

According to the literature, the content of tPA is 5-10 ng/mL under normal physiological conditions[35], while in the case of strenuous exercise or venous congestion, the content of tPA in the body increases from 20 times to 100 times, that is, over 100 ng/mL[36]. Therefore, the dose of tPA used in this experiment is 125 ng/mL to mimic the naturally occurring tPA content in the case of in vivo thrombosis.

Figure 10:
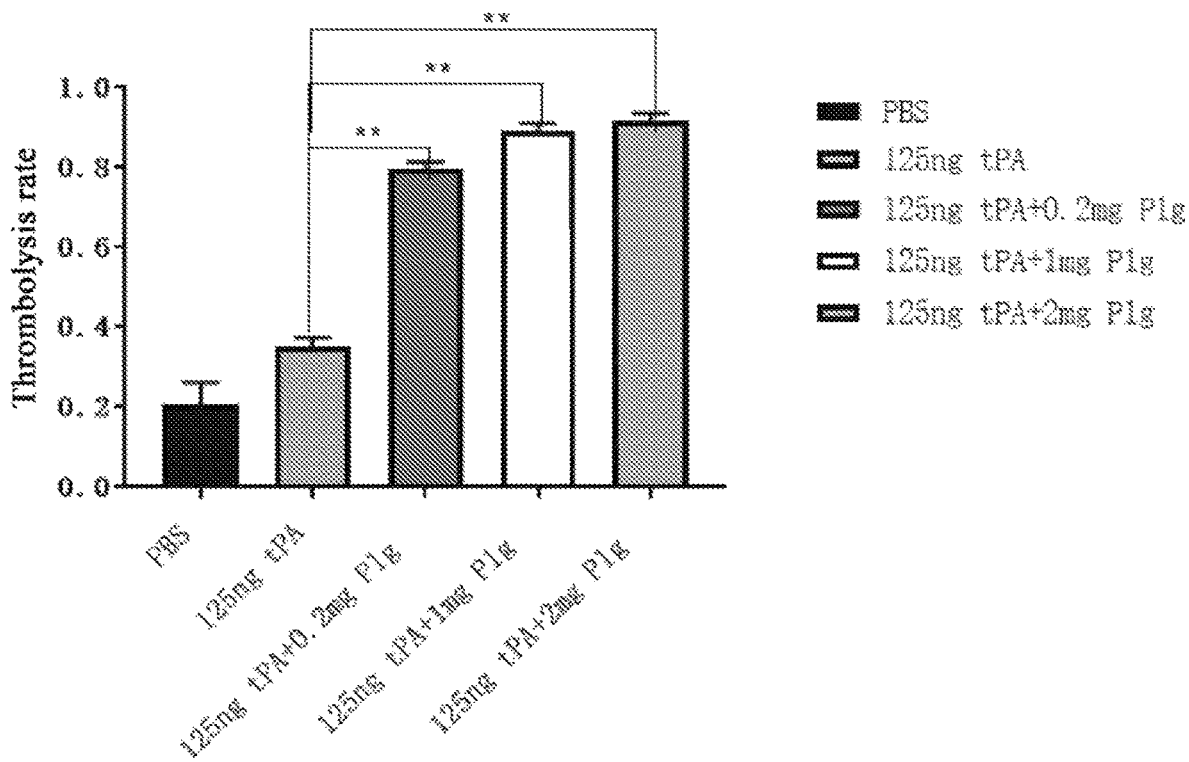
FIG. 10 shows the thrombolytic effect of different doses of plasminogen on 30-minute fresh thrombus when incubated at 37° C. for 2 hours at 125 ng tPA.

This experiment shows that for fresh thrombi formed in vitro for 30 minutes, the thrombolysis rate shows a gradient increase trend under the condition of gradient increase of plasminogen dose. In addition, the thrombolysis rates in each plasminogen group are higher than those in the control group where tPA alone is added, and the statistical differences are extremely significant. These results indicate that in the case of naturally occurring tPA levels in the presence of thrombosis in the body, the addition of 0.2 mg or more of plasminogen for 1 hour can significantly promote thrombolysis (FIG. 10). It is demonstrated that plasminogen can not only promote the dissolution of old thrombus, but also promote the dissolution of fresh thrombus.

Example 12 Plasminogen Promotes Dissolution of Microthrombus Caused by Diabetes

Ten 24-25-week-old db/db male mice are randomly divided into two groups, solvent PBS-treated control group and plasminogen-treated group. 5 mice per group. The day starting the experiment is recorded as day 0 when mice are weighed and grouped. The second day of the experiment when starting administration of plasminogen or PBS is recorded as day 1. The continuous administration is performed for 15 days. The mice in the plasminogen-treated group are injected with plasminogen at a dose of 2 mg/0.2 mL/body/day through tail vein, and those in the solvent PBS-treated control group are administered the same volume of PBS. On the 16th day, eyeballs are taken to draw blood and after the whole blood is left standing, serum is used to detect D-dimer content in blood.

Figure 11:
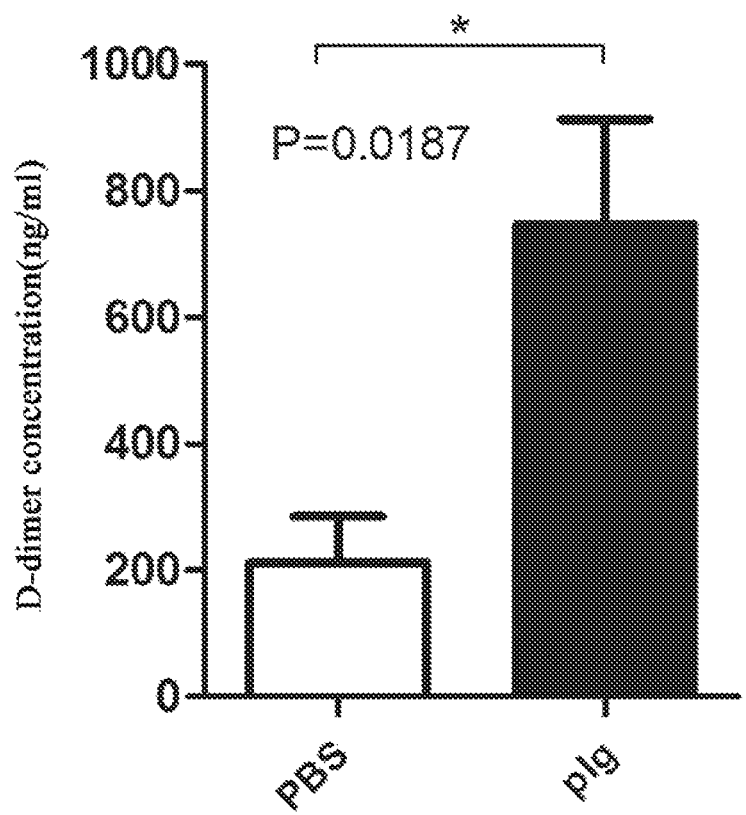
FIG. 11 shows the results of detection of the concentration of D-dimer in serum after 15 days of plasminogen administration in 24-25 weeks old diabetic mice.

The results show that after 15 days of administration, the content of D-dimer in the plasminogen-treated group is significantly increased (FIG. 11), suggesting that the microthrombus caused by diabetes is significantly dissolved after the administration of plasminogen.

Example 13 Plasminogen Promotes Thrombolysis in Cardiac Tissue in Late-Stage Diabetic Mice Ten 24-25-week-old db/db male mice are randomly divided into two groups, solvent PBS-treated control group and plasminogen-treated group. 5 mice per group. The day starting the experiment is recorded as day 0 when mice are weighed and grouped. The second day of the experiment when starting administration of plasminogen or PBS is recorded as day 1. The continuous administration is performed for 31 days. The mice in the plasminogen-treated group are injected with plasminogen at a dose of 2 mg/0.2 mL/body/day through tail vein, and those in the solvent PBS-treated control group are administered the same volume of PBS. Mice are sacrificed on day 32 and hearts are collected and fixed in 10% neutral formalin for 24 hours. The fixed cardiac tissue is dehydrated in gradient ethanol and cleared in xylene, followed by being paraffin-embedded. The thickness of the tissue section is 5 After dewaxing and rehydration, the sections are washed with water once, incubated with 3% hydrogen peroxide for 15 minutes, and washed with water twice for 5 minutes each time. Block with 10% normal sheep serum (Vector laboratories, Inc., USA) for 1 hour; then discard the sheep serum and circle the tissue with a PAP pen. Incubate with rabbit anti-mouse fibrinogen antibody (Abcam) at 4□ overnight and wash with TBS twice for 5 minutes each time. Incubate with the secondary antibody, goat anti-rabbit IgG (HRP) antibody (Abcam) for 1 hour at room temperature and wash with TBS twice for 5 minutes each time. Stain according to DAB kit (Vector laboratories, Inc., USA), counterstain with hematoxylin for 30 seconds after washing with water 3 times and flush with water for 5 minutes. Gradient dehydration, clearing and mounting are followed. Sections are observed under a microscope at 400 times.

Fibrinogen is a precursor of fibrin. In the presence of tissue damage, as a stress response to the body's damage, fibrinogen is hydrolyzed into fibrin[40-42], so fibrin level can be used as a sign of the degree of damage. Fibrin is also a major component of thrombus formed after tissue damage. Therefore, fibrin level can also be used as a marker of thrombus.

Figure 12:
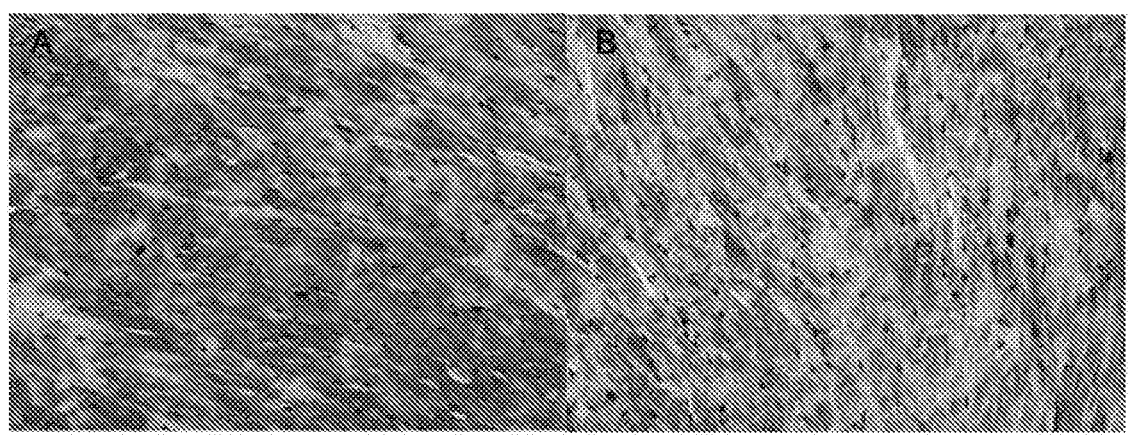
FIG. 12 shows cardiac fibrin immunohistochemical staining results after 31 days of PBS (A) or plasminogen (B) administration in 24-25 weeks old diabetic mice.

The results show that compared with the solvent PBS-treated control group (FIG. 12A), the plasminogen-treated group (FIG. 12B) has a lighter positive staining of fibrin in cardiac tissue of mice, indicating the reduction of fibrin deposition in the cardiac tissue of the plasminogen-treated group, which reflects that plasminogen can promote the repair of cardiac tissue damage caused by diabetes, and it also demonstrates that plasminogen can promote the dissolution of cardiac tissue thrombus.

Example 14 Plasminogen Promotes Thrombolysis in Renal Tissue in Late-Stage Diabetic Mice Twenty 24-25-week-old db/db male mice are randomly divided into two groups, solvent PBS-treated control group and plasminogen-treated group. 10 mice per group. The day starting the experiment is recorded as day 0 when mice are weighed and grouped. The second day of the experiment when starting administration of plasminogen or PBS is recorded as day 1. The continuous administration is performed for 31 days. The mice in the plasminogen-treated group are injected with plasminogen at a dose of 2 mg/0.2 mL/body/day through tail vein, and those in the solvent PBS-treated control group are administered the same volume of PBS. Mice are sacrificed on day 32 and kidneys are collected and fixed in 10% neutral formalin for 24 hours. The fixed renal tissue is dehydrated in gradient ethanol and cleared in xylene, followed by being paraffin-embedded. The thickness of the tissue section is 5 μm. After dewaxing and rehydration, the sections are washed with water once, incubated with 3% hydrogen peroxide for 15 minutes, and washed with water twice for 5 minutes each time. Block with 10% normal sheep serum (Vector laboratories, Inc., USA) for 1 hour; when time is up, discard the sheep serum and circle the tissue with a PAP pen. Incubate with rabbit anti-mouse fibrinogen antibody (Abcam) at 4□ overnight and wash with TBS twice for 5 minutes each time. Incubate with the secondary antibody, goat anti-rabbit IgG (HRP) antibody (Abcam) for 1 hour at room temperature and wash with TBS twice for 5 minutes each time. Stain according to DAB kit (Vector laboratories, Inc., USA), counterstain with hematoxylin for 30 seconds after washing with water 3 times and flush with water for 5 minutes. Gradient dehydration, clearing and mounting are followed. Sections are observed under a microscope at 200 times.

Fibrinogen is a precursor of fibrin. In the presence of tissue damage, as a stress response to the body's damage, fibrinogen is hydrolyzed into fibrin[40-42], so fibrin level can be used as a sign of the degree of damage. Fibrin is also a major component of thrombus formed after tissue damage. Therefore, fibrin level can also be used as a marker of thrombus.

Figure 13:
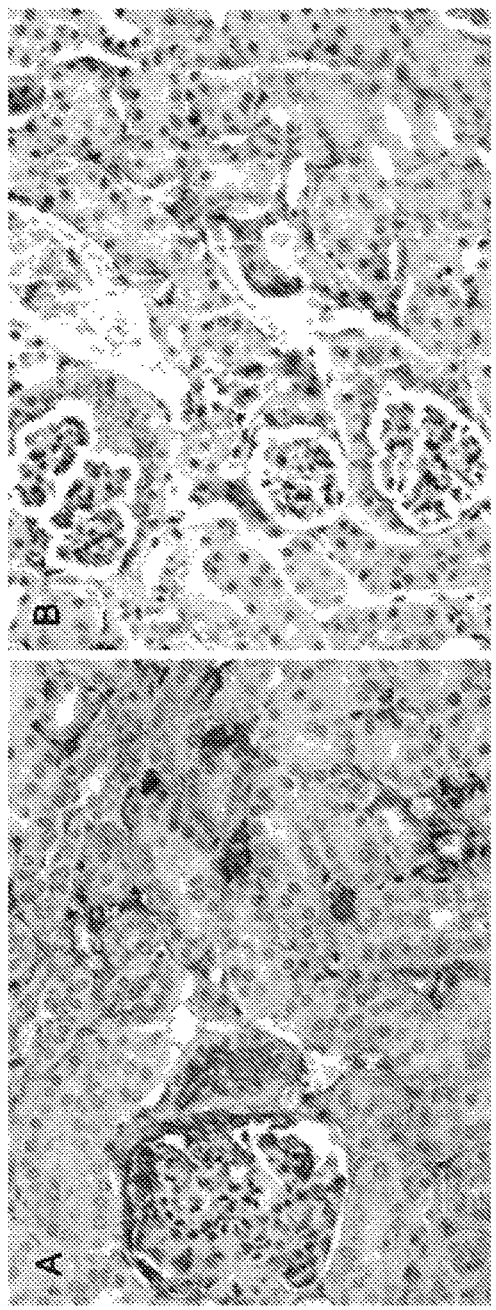
FIG. 13 shows renal fibrin immunohistochemical staining results after 31 days of PBS (A) or plasminogen (B) administration in 24-25 weeks old diabetic mice.

The results show that the plasminogen-treated group (FIG. 13B) has a lighter positive staining of fibrinogen than the solvent PBS-treated control group (FIG. 13A). It indicates that injection of plasminogen can significantly reduce renal fibrin deposition in diabetic mice, which shows that plasminogen has significant repair effect on kidney damage in diabetic mice, and it also demonstrates that plasminogen can promote the dissolution of renal tissue thrombus.

Example 15 Plasminogen Promotes Thrombolysis in Liver Tissue in Late-Stage Diabetes Ten 24-25-week-old db/db male mice are randomly divided into two groups, solvent PBS-treated control group and plasminogen-treated group. 5 mice per group. The day starting the experiment is recorded as day 0 when mice are weighed and grouped. The second day of the experiment when starting administration of plasminogen or PBS is recorded as day 1. The continuous administration is performed for 31 days. The mice in the plasminogen-treated group are injected with plasminogen at a dose of 2 mg/0.2 mL/body/day through tail vein, and those in the solvent PBS-treated control group are administered the same volume of PBS. Mice are sacrificed on day 32 and livers are collected and fixed in 10% neutral formalin for 24 hours. The fixed liver tissue is dehydrated in gradient ethanol and cleared in xylene, followed by being paraffin-embedded. The thickness of the tissue section is 5 After dewaxing and rehydration, the sections are washed with water once, incubated with 3% hydrogen peroxide for 15 minutes, and washed with water twice for 5 minutes each time. Block with 10% normal sheep serum (Vector laboratories, Inc., USA) for 1 hour; when time is up, discard the sheep serum and circle the tissue with a PAP pen. Incubate with rabbit anti-mouse fibrinogen antibody (Abcam) at 4□ overnight and wash with TBS twice for 5 minutes each time. Incubate with the secondary antibody, goat anti-rabbit IgG (HRP) antibody (Abcam) for 1 hour at room temperature and wash with TBS twice for 5 minutes each time. Stain according to DAB kit (Vector laboratories, Inc., USA), counterstain with hematoxylin for 30 seconds after washing with water 3 times and flush with water for 5 minutes. Gradient dehydration, clearing and mounting are followed. Sections are observed under a microscope at 200 times.

Fibrinogen is a precursor of fibrin. In the presence of tissue damage, as a stress response to the body's damage, fibrinogen is hydrolyzed into fibrin[40-42], so fibrin level can be used as a sign of the degree of damage. Fibrin is also a major component of thrombus formed after tissue damage. Therefore, fibrin level can also be used as a marker of thrombus.

Figure 14:
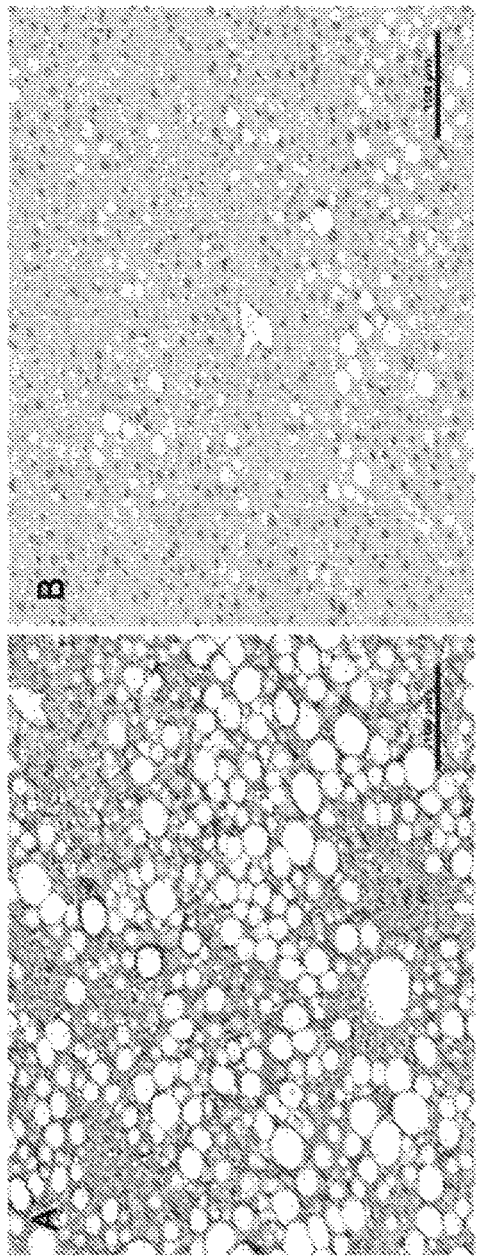
FIG. 14 shows liver fibrin immunohistochemical staining results after 31 days of PBS (A) or plasminogen (B) administration in 24-25 weeks old diabetic mice.

The study finds that compared with the solvent PBS-treated control group (FIG. 14A), the plasminogen-treated group (FIG. 14B) has a lighter positive staining of fibrin in liver tissue of mice, indicating that injection of plasminogen can significantly reduce liver fibrin deposition in diabetic mice, which reflects that plasminogen has significant repair effect on liver damage in diabetic mice, and it also demonstrates that plasminogen can promote the dissolution of liver tissue thrombus.

Example 16 Plasminogen Promotes Thrombolysis in Nerve Tissue in Mice with Late-Stage Diabetic Nerve Damage Ten 24-25-week-old db/db male mice are randomly divided into two groups, solvent PBS-treated control group and plasminogen-treated group. 5 mice per group. The day starting the experiment is recorded as day 0 when mice are weighed and grouped. The second day of the experiment when starting administration of plasminogen or PBS is recorded as day 1. The continuous administration is performed for 15 days. The mice in the plasminogen-treated group are injected with plasminogen at a dose of 2 mg/0.2 mL/body/day through tail vein, and those in the solvent PBS-treated control group are administered the same volume of PBS. Mice are sacrificed on day 16 and sciatic nerves are collected and fixed in 10% neutral formalin for 24 hours. The fixed sciatic nerve is dehydrated in gradient ethanol and cleared in xylene, followed by being paraffin-embedded. The thickness of the tissue section is 5 After dewaxing and rehydration, the sections are washed with water once and then the tissues are circled with a PAP pen. Incubate with 3% TBS diluted hydrogen peroxide for 15 minutes and wash with water 3 times. Block with 10% normal sheep serum (Vector laboratories, Inc., USA) for 1 hour and absorb excess serum. Incubate with rabbit anti-mouse fibrinogen antibody (Abcam) at room temperature for 1 hour or at 4□ overnight and wash with TBS 3 times. Incubate with the secondary antibody, goat anti-rabbit IgG (HRP) antibody (Abcam) for 1 hour at room temperature and wash with TBS 3 times. Stain according to DAB kit (Vector laboratories, Inc., USA), counterstain with hematoxylin for 30 seconds after washing with water 3 times and flush with water for 5 minutes. Gradient dehydration, clearing and mounting are followed. Sections are observed under a microscope at 400 times.

Fibrinogen is a precursor of fibrin. In the presence of tissue damage, as a stress response to the body's damage, fibrinogen is hydrolyzed into fibrin[40-42], so fibrin level can be used as a sign of the degree of damage. Fibrin is also a major component of thrombus formed after tissue damage. Therefore, fibrin level can also be used as a marker of thrombus.

Figure 15:
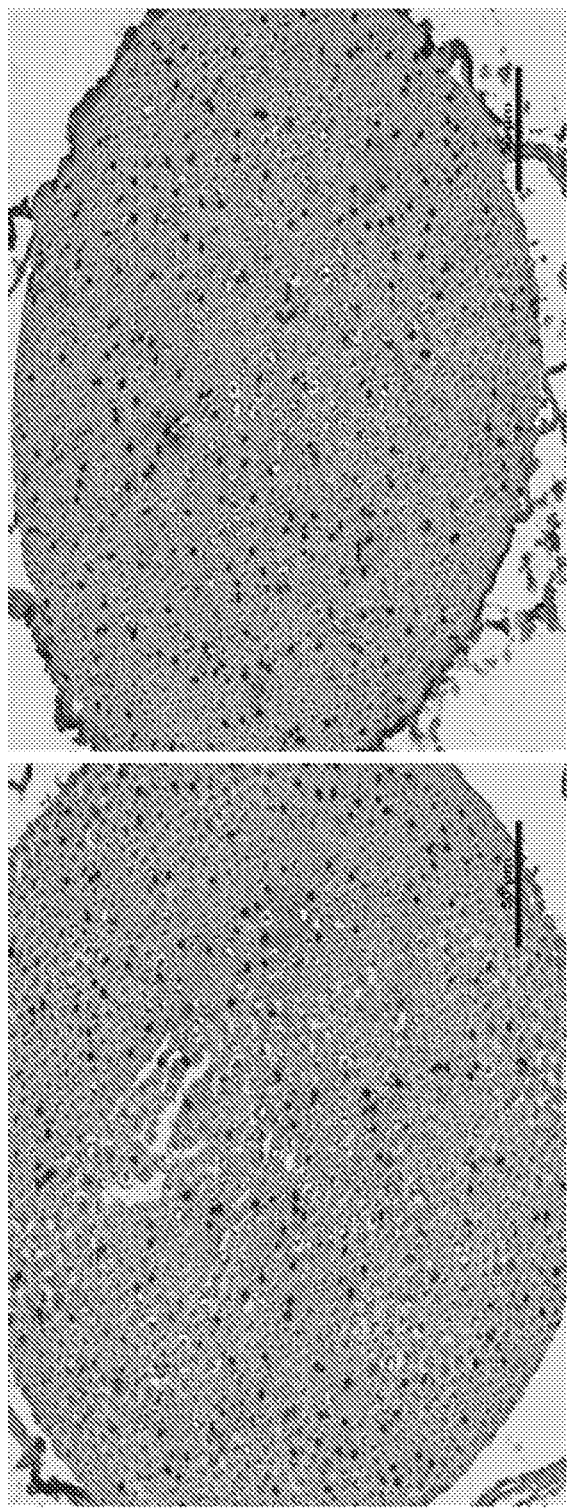
FIG. 15 shows sciatic nerve fibrin immunohistochemical staining after 15 days of PBS (A) or plasminogen (B) administration in 24-25 weeks old mice with late diabetic nerve damage.

The study finds that compared with the solvent PBS-treated control group (FIG. 15A), the sciatic nerve fibrin levels are reduced in mice in the plasminogen-treated group (FIG. 15B), indicating that plasminogen has the function of degrading fibrin levels and the damage is repaired to a certain extent, which also demonstrates that plasminogen can promote the dissolution of thrombi around nerve tissue.

Summary of Experimental Results

Experiments in the embodiments of the present invention include two parts of in vitro thrombolysis and in vivo thrombolysis of plasminogen.

In vitro thrombolysis mimics the conditions of in vivo thrombolysis. 10 ng/mL tPA is selected to mimic the naturally occurring tPA levels in the body under normal physiological conditions, and 125 ng/mL tPA is selected to mimic the naturally occurring tPA levels in the case of thrombosis in the body, to study plasminogen thrombolytic capacity.

The experimental study of the present invention shows that under the condition of 10 ng/mL tPA or 125 ng/mL tPA, plasminogen has very good thrombolytic effect whether it is a 20-hour old thrombus or a 72-hour old thrombus. And with the increase of plasminogen dose, the thrombolytic efficiency increases.

Plasminogen has a strong ability to dissolve fresh thrombus, and the thrombolysis rate can reach over 80% after two hours of incubation.

We also study the thrombolytic effect of plasminogen in the presence of uPA. Under the conditions of 1 ng/mL uPA or 100 ng/mL uPA, plasminogen also has very good thrombolytic effect. And with the increase of plasminogen dose, the thrombolytic efficiency increases.

In the experiments in vivo, late-stage diabetic mice are administered 2 mg of plasminogen daily for 15 consecutive days and the D-dimer content in the serum is significantly increased. At the same time, the fibrin levels of heart, liver, kidney and nerve tissues significantly decrease, indicating that plasminogen can obviously promote the dissolution of thrombi caused by diabetes-induced damage in these tissues and fibrin degradation, which proves that the administration of plasminogen to experimental animals can also achieve significant thrombolytic effect.

The mouse jugular vein thrombosis model experiment shows that plasminogen can bind to thrombus in vivo very specifically.

In addition, our study showed that thrombolysis of plasminogen is more moderate than that of tPA, and tail-bleeding experiments in mice showed no bleeding side effects of plasminogen.

In summary, plasminogen has a very good thrombolytic capacity, especially for the old thrombus, and has the characteristics of high specificity, moderate strength, quick effect and no bleeding side effects.

REFERENCES

[1] Yuan guiqing, Thrombotic disease has become an important disease that threatens human health and life. Chinese Journal of Laboratory Medicine, 2004, 8(27)487.
[2] Alexander C M and Werb, Z. (1991). Extracellular matrix degradation. In Cell Biology of Extracellular Matrix, Hay E D, ed. (New York: Plenum Press), pp. 255-302.
[3] Werb, Z., Mainardi, C. L., Vater, C. A., and Harris, E. D., Jr. (1977). Endogenous activiation of latent collagenase by rheumatoid synovial cells. Evidence for a role of plasminogen activator. N. Engl. J. Med. 296, 1017-1023.
[4] He, C. S., Wilhelm, S. M., Pentland, A. P., Marmer, B. L., Grant, G. A., Eisen, A. Z., and Goldberg, G. I. (1989). Tissue cooperation in a proteolytic cascade activating human interstitial collagenase. Proc. Natl. Acad. Sci. U. S. A 86, 2632-2636.
[5] Stoppelli, M. P., Corti, A., Soffientini, A., Cassani, G., Blasi, F., and Assoian, R. K. (1985). Differentiation-enhanced binding of the amino-terminal fragment of human urokinase plasminogen activator to a specific receptor on U937 monocytes. Proc. Natl. Acad. Sci. U. S. A 82, 4939-4943.
[6] Vassalli, J. D., Baccino, D., and Belin, D. (1985). A cellular binding site for the Mr 55,000 form of the human plasminogen activetor, urokinase. J. Cell Biol. 100, 86-92.
[7] Wiman, B. and Wallen, P. (1975). Structural relationship between "glutamic acid" and "lysine" forms of human plasminogen and their interaction with the NH2-terminal activation peptide as studied by affinity chromatography. Eur. J. Biochem. 50, 489-494.
[8] Saksela, O. and Rifkin, D. B. (1988). Cell-associated plasminogen activation: regulation and physiological functions. Annu. Rev. Cell Biol. 4, 93-126
[9] Raum, D., Marcus, D., Alper, C. A., Levey, R., Taylor, P. D., and Starzl, T. E. (1980). Synthesis of human plasminogen by the liver. Science 208, 1036-1037
[10] Wallen P (1980). Biochemistry of plasminogen. In Fibrinolysis, Kline D L and Reddy K K N, eds.
[11] Sottrup-Jensen, L., Zaj del, M., Claeys, H., Petersen, T. E., and Magnusson, S. (1975). Amino-acid sequence of activation cleavage site in plasminogen: homology with "pro" part of prothrombin. Proc. Natl. Acad. Sci. U. S. A 72, 2577-2581.
[12] Collen, D. and Lijnen, H. R. (1991). Basic and clinical aspects of fibrinolysis and thrombolysis. Blood 78, 3114-3124.
[13] Alexander, C. M. and Werb, Z. (1989). Proteinases and extracellular matrix remodeling. Curr. Opin. Cell Biol. 1, 974-982. [14] Mignatti, P. and Rifkin, D. B. (1993). Biology and biochemistry of proteinases in tumor invasion. Physiol Rev. 73, 161-195.
[15] Collen, D. (2001). Ham-Wasserman lecture: role of the plasminogen system in fibrin-homeostasis and tissue remodeling. Hematology. (Am. Soc. Hematol. Educ. Program.) 1-9.
[16] Rifkin, D. B., Moscatelli, D., Bizik, J., Quarto, N., Blei, F., Dennis, P., Flaumenhaft, R., and Mignatti, P. (1990). Growth factor control of extracellular proteolysis. Cell Differ. Dev. 32, 313-318.
[17] Andreasen, P. A., Kjoller, L., Christensen, L., and Duffy, M. J. (1997). The urokinase-type plasminogen activator system in cancer metastasis: a review. Int. J. Cancer 72, 1-22.
[18] Rifkin, D. B., Mazzieri, R., Munger, J. S., Noguera, I., and Sung, J. (1999). Proteolytic control of growth factor availability. APMIS 107, 80-85.
[19] Hillis L D, et. al. High dose intravenous streptokinase for acute myocardial infarction: preliminary results of a multicenter trial. J Am Coll Cardiol. 1985; 6:957-962.
[20] Smalling R W. A fresh look at the molecular pharmacology of plasminogen activators: from theory to test tube to clinical outcomes. Am J Health-Syst Pharm 1997; 54(suppl 1):S17-S22.
[21] Nobel S, McTavish D. Reteplase: a review of it pharmacological properties and clinical efficiency in the management of acute myocardial infarction. [J]. Drug, 1996, 52(4):589-605.
[22] Abdoli-Nasab Ml, Jalali-Javaran M, Expression of the truncated tissue plasminogen activator (K2S) gene in tobacco chloroplast, Mol Biol Rep (2013) 40:5749-5758
[23] Gottlob R. (1975) Plasminogen and plasma inhibitors inarterial and venous thrombi of various ages. In: Progress inchemical fibrinolysis and thrombolysis. vol. 1. Raven Press, New York, pp. 23-36.
[24] Sabovic M, Lijnen H R, Keber D, Collen D. (1989) Effect ofretraction on the lysis of human clots with fibrin specific andnon-fibrin specific plasminogen activators. Thromb Haemost, 62, 1083-1087.
[25] Potter van Loon B J, Rijken D C, Brommer E J, van der MaasAP. (1992) The amount of plasminogen, tissue-type plasminogen activator and plasminogen activator inhibitor type 1 in human thrombi and the relation to ex-vivo lysibility. Thromb Haemost, 67, 101-105.
[26] Hacke W, Kaste M, Bluhmki E, Brozman M, Dávalos A et al. (2008) Thrombolysis with alteplase 3 to 4.5 hours after acute ischemic stroke. N Engl J Med 359: 1317-1329.
[27] Lees K R, Bluhmki E, von Kummer R, Brott T G, Toni D et al. (2010) Time to treatment with intravenous alteplase and outcome in stroke: anupdated pooled analysis of Ecass, Atlantis, Ninds, and Epithet trials. Lancet 375.
[28] Marder V J, Novokhatny V. Direct fibrinolytic agents: biochemical attributes, preclinical foundation and clinical potential [J]. Journal of Thrombosis and Haemostasis, 2010, 8(3): 433-444.
[29] Hunt J A, Petteway Jr S R, Scuderi P, et al. Simplified recombinant plasmin: production and fu-nctional comparison of a novel thrombolytic molecule with plasma-derived plasmin [J]. Thromb Haemost, 2008, 100(3): 413-419.
[30] Sottrup-Jensen L, Claeys H, Zajdel M, et al. The primary structure of human plasminogen: Isolation of two lysine-binding fragments and one "mini"-plasminogen (MW, 38,000) by elastase-catalyzed-specific limited proteolysis [J]. Progress in chemical fibrinolysis and thrombolysis, 1978, 3: 191-209.
[31] Nagai N, Demarsin E, Van Hoef B, et al. Recombinant human microplasmin: production and potential therapeutic properties [J]. Journal of Thrombosis and Haemostasis, 2003, 1(2): 307-313.
[32] Valery V. Novokhatny, Gary J. Jesmok, Locally delivered plasmin: why should it be superior to plasminogen activators for direct thrombolysis, Trends in Pharmacological Sciences Vol. 25 No. 2 Feb. 2004
[33] V. Novokhatny, K. Talylor and T. P. Zimmerman, Thrombolytic potency of acid-stabilized plasmin: superiority over tissue-type plasminogen activator in an in vitro model of catheter-assisted thrombolysis, Journal of Thrombosis and Haemostasis, 1: 1034-1041
[34] F Bachmann, Springer, Fibrinolytics and antifibrinolytics, 2001, 146(4):670
[35] R. B. Aisinal and L. I. Mukhametova, Structure and Function of Plasminogen/Plasmin System, Russian Journal of Bioorganic Chemistry, 2014, Vol. 40, No. 6, pp. 590-605.
[36] Kyle Landskroner, M S, Neil Olson, D V M, PhD, and Gary Jesmok, PhD, Cross-Species Pharmacologic Evaluation of Plasmin as a Direct-Acting Thrombolytic Agent: Ex Vivo Evaluation for Large Animal Model Development, J Vasc Intery Radiol 2005; 16:369-377.
[37] Edvin L. Madison, Gary S. Coombs, and Dacid R. Corey, Substrate Specificity of Tissue Type Plasminogen Activator, The Journal of biological, Chemistry, 1995, Vol. 270, No. 13, pp. 7558-7562.
[38] Kei Takahashi, Hau C. Kwaan, Enki Koh, ardMasatakaTanabe, Enzymatic Properties Of The Phosphorylated Urokinase-Type Plasminogen Activator Isolated From A Human Carcinomatous Cell Line, Biochemical and Biophysical Research Communications, 1992 Pages 1473-1481
[39] Hui Y H, Huang N H, Ebbert L et al. Pharmacokinetic comparisons of tail-bleeding with cannula- or retro-orbital bleeding techniques in rats using six marketed drugs. J Pharmacol Toxicol Methods. 2007 September-October; 56(2):256-64.
[40] Jae Kyu Ryu, Mark A. Petersen, Sara G. Murray et al. Blood coagulation protein fibrinogen promotes autoimmunity and demyelination via chemokine release and antigen presentation. Nature Communications, 2015, 6:8164.
[41] Dimitrios Davalos, Katerina Akassoglou. Fibrinogen as a key regulator of inflammation in disease. Seminars in Immunopathology, 2012. 34(1):43-62.
[42] Valvi D, Mannino D M, Mullerova H, et al. Fibrinogen, chronic obstructive pulmonary disease (COPD) and outcomes in two United States cohorts. Int J Chron Obstruct Pulmon Dis 2012; 7:173-82.

The invention claimed is:

1. A method of preventing and/or eliminating an arterial and venous thrombosis in a subject, comprising administering to the subject an effective amount of plasminogen alone.

2. The method according to claim 1, wherein said thrombus comprises fresh thrombus and old thrombus.

3. The method of claim 1, wherein the thrombosis is a thrombosis caused by a disease selected from the group consisting of a blood system disease, a circulatory system disease, an autoimmune disease, a metabolic disorder disease and an infectious disease.

4. The method of claim 1, wherein the thrombosis is a large vascular thrombosis, small vascular thrombosis or microvascular thrombosis, secondary to diabetes.

5. The method of claim 1, wherein the thrombosis is a thrombosis caused by large and/or small vascular lesions.

6. A method of preventing and/or treating thrombosis-related diseases in a subject, comprising administering to the subject an effective amount of plasminogen alone, wherein the plasminogen prevents and/or treats the thrombosis-related disease in the subject by eliminating the thrombus.

7. The method according to claim 6, wherein the thrombosis-related disease comprises a disease selected from the group consisting of pancreatitis and cirrhosis caused by portal vein thrombosis; renal embolism caused by renal vein thrombosis; systemic sepsis, pulmonary embolism, cerebral thrombosis and deep vein thrombosis caused by internal jugular vein thrombosis; organ infarction caused by arterial or venous thrombosis.

8. The method according to claim 6, wherein the thrombosis-related disease comprises a disease selected from the group consisting of diabetic nephropathy, diabetic retinopathy, diabetic liver disease, diabetic heart disease, diabetic enteropathy and diabetic neuropathy.

9. The method according to claim 1, wherein the plasminogen is administered in combination with a therapeutic drug for other diseases accompanying the thrombosis.

10. The method according to claim 1, wherein the plasminogen is a protein having at least 80%, 85%, 90%, 95%, 96%, 97%, 98% or 99% sequence identity with the SEQ ID No.2, 6, 8, 10 or 12 and retaining a plasminogen activity.

11. The method according to claim 7, wherein the organ infarction caused by arterial or venous thrombosis comprises a disease selected from the group consisting of cerebral infarction, myocardial infarction, thrombotic stroke, atrial fibrillation, unstable angina pectoris, intractable angina pectoris, transient ischemic attack and pulmonary embolism.

\* \* \* \* \*

SEQUENCE LISTING

```
<160> NUMBER OF SEQ ID NOS: 14

<210> SEQ ID NO 1
<211> LENGTH: 2376
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for the natural
      human plasminogen(Glu-PLG,Glu-plasminogen) without the
      signal peptide

<400> SEQUENCE: 1
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
```

```
ctctcagagt gcaagactgg gaatggaaag aactacagag ggacgatgtc caaaacaaaa      300
aatggcatca cctgtcaaaa atggagttcc acttctcccc acagacctag attctcacct      360
gctacacacc cctcagaggg actggaggag aactactgca ggaatccaga caacgatccg      420
caggggccct ggtgctatac tactgatcca gaaaagagat atgactactg cgacattctt      480
gagtgtgaag aggaatgtat gcattgcagt ggagaaaact atgacggcaa atttccaag       540
accatgtctg gactggaatg ccaggcctgg gactctcaga gcccacacgc tcatggatac      600
attccttcca aatttccaaa caagaacctg aagaagaatt actgtcgtaa ccccgatagg      660
gagctgcggc cttggtgttt caccaccgac cccaacaagc gctgggaact ttgtgacatc      720
ccccgctgca caacacctcc accatcttct ggtcccacct accagtgtct gaagggaaca      780
ggtgaaaaact atcgcgggaa tgtggctgtt accgtgtccg gcacacctg tcagcactgg       840
agtgcacaga cccctcacac acataacagg acaccagaaa acttcccctg caaaaatttg      900
gatgaaaact actgccgcaa tcctgacgga aaaagggccc catggtgcca tacaaccaac      960
agccaagtgc ggtgggagta ctgtaagata ccgtcctgtg actcctcccc agtatccacg     1020
gaacaattgg ctcccacagc accacctgag ctaaccccctg tggtccagga ctgctaccat     1080
ggtgatggac agagctaccg aggcacatcc tccaccacca ccacaggaaa gaagtgtcag     1140
tcttggtcat ctatgacacc acaccggcac cagaagaccc cagaaaacta cccaaatgct     1200
ggcctgacaa tgaactactg caggaatcca gatgccgata aaggcccctg tgtttttacc     1260
acagacccca cgtcaggtg ggagtactgc aacctgaaaa aatgctcagg aacagaagcg      1320
agtgttgtag cacctccgcc tgttgtcctg cttccagatg tagagactcc ttccgaagaa     1380
gactgtatgt ttgggaatgg gaaaggatac cgaggcaaga gggcgaccac tgttactggg     1440
acgccatgcc aggactgggc tgcccaggag ccccatagac acagcatttt cactccagag     1500
acaaatccac gggcgggtct ggaaaaaaat tactgccgta accctgatgg tgatgtaggt     1560
ggtccctggt gctacacgac aaatccaaga aaactttacg actactgtga tgtccctcag     1620
tgtgcggccc cttcatttga ttgtgggaag cctcaagtgg agccgaagaa atgtcctgga     1680
agggttgtag gggggtgtgt ggcccaccca cattcctggc cctggcaagt cagtcttaga     1740
acaaggtttg gaatgcactt ctgtggaggc accttgatat ccccagagtg ggtgttgact     1800
gctgcccact gcttggagaa gtccccaagg ccttcatcct acaaggtcat cctgggtgca     1860
caccaagaag tgaatctcga accgcatgtt caggaaatag aagtgtctag gctgttcttg     1920
gagcccacac gaaaagatat tgccttgcta agctaagca gtcctgccgt catcactgac       1980
aaagtaatcc cagcttgtct gccatcccca aattatgtgg tcgctgaccg gaccgaatgt     2040
ttcatcactg gctggggaga aacccaaggt acttttggag ctggccttct caaggaagcc     2100
cagctccctg tgattgagaa taaagtgtgc aatcgctatg agtttctgaa tggaagagtc     2160
caatccaccg aactctgtgc tgggcatttg gccggaggca ctgacagttg ccaggtgac      2220
agtggaggtc ctctggtttg cttcgagaag gacaaataca ttttacaagg agtcacttct     2280
tggggtcttg gctgtgcacg ccccaataag cctggtgtct atgttcgtgt ttcaaggttt     2340
gttacttgga ttgagggagt gatgagaaat aattaa                               2376
```

<210> SEQ ID NO 2
<211> LENGTH: 791
<212> TYPE: PRT
<213> ORGANISM: Artificial Sequence
<220> FEATURE:

<223> OTHER INFORMATION: Description of Artificial Sequence: Synthetic
polypeptide
<220> FEATURE:
<223> OTHER INFORMATION: Amino acid sequence of the natural human
plasminogen(Glu-PLG,Glu-plasminogen)without the
signal peptide

<400> SEQUENCE: 2

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
        355                 360                 365

Thr Ser Ser Thr Thr Thr Thr Gly Lys Lys Cys Gln Ser Trp Ser Ser
```

```
              370                 375                 380
Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
        435                 440                 445

Val Leu Leu Pro Asp Val Glu Thr Pro Ser Glu Glu Asp Cys Met Phe
    450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
        515                 520                 525

Pro Arg Lys Leu Tyr Asp Tyr Cys Asp Val Pro Gln Cys Ala Ala Pro
    530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
        595                 600                 605

Pro Arg Pro Ser Ser Tyr Lys Val Ile Leu Gly Ala His Gln Glu Val
    610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
            660                 665                 670

Val Val Ala Asp Arg Thr Glu Cys Phe Ile Thr Gly Trp Gly Glu Thr
        675                 680                 685

Gln Gly Thr Phe Gly Ala Gly Leu Leu Lys Glu Ala Gln Leu Pro Val
    690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
            740                 745                 750

Tyr Ile Leu Gln Gly Val Thr Ser Trp Gly Leu Gly Cys Ala Arg Pro
        755                 760                 765

Asn Lys Pro Gly Val Tyr Val Arg Val Ser Arg Phe Val Thr Trp Ile
    770                 775                 780

Glu Gly Val Met Arg Asn Asn
785                 790
```

<210> SEQ ID NO 3
<211> LENGTH: 2433
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Nucleotide sequence coding for the natural
plasminogen (from swiss prot)with the signal peptide

<400> SEQUENCE: 3

| | | | | | |
|---|---|---|---|---|---|
| atggaacata | aggaagtggt | tcttctactt | cttttatttc | tgaaatcagg | tcaaggagag | 60 |
| cctctggatg | actatgtgaa | tacccagggg | gcttcactgt | tcagtgtcac | taagaagcag | 120 |
| ctgggagcag | aagtataga | agaatgtgca | gcaaaatgtg | aggaggacga | agaattcacc | 180 |
| tgcagggcat | tccaatatca | cagtaaagag | caacaatgtg | tgataatggc | tgaaaacagg | 240 |
| aagtcctcca | taatcattag | gatgagagat | gtagttttat | ttgaaaagaa | agtgtatctc | 300 |
| tcagagtgca | agactgggaa | tggaaagaac | tacagaggga | cgatgtccaa | aacaaaaaat | 360 |
| ggcatcacct | gtcaaaaatg | gagttccact | tctcccccaca | gacctagatt | ctcacctgct | 420 |
| acacacccct | cagagggact | ggaggagaac | tactgcagga | atccagacaa | cgatccgcag | 480 |
| gggccctggt | gctatactac | tgatccagaa | aagagatatg | actactgcga | cattcttgag | 540 |
| tgtgaagagg | aatgtatgca | ttgcagtgga | gaaaactatg | acggcaaaat | ttccaagacc | 600 |
| atgtctggac | tggaatgcca | ggcctggac | tctcagagcc | cacacgctca | tggatacatt | 660 |
| ccttccaaat | ttccaaacaa | gaacctgaag | aagaattact | gtcgtaaccc | cgataggag | 720 |
| ctgcggcctt | ggtgtttcac | caccgacccc | aacaagcgct | gggaactttg | tgacatcccc | 780 |
| cgctgcacaa | cacctccacc | atcttctggt | cccacctacc | agtgtctgaa | gggaacaggt | 840 |
| gaaaactatc | gcgggaatgt | ggctgttacc | gtgtccgggc | acacctgtca | gcactggagt | 900 |
| gcacagaccc | ctcacacaca | taacaggaca | ccagaaaact | tcccctgcaa | aaatttggat | 960 |
| gaaaactact | gccgcaatcc | tgacggaaaa | agggccccat | ggtgccatac | aaccaacagc | 1020 |
| caagtgcggt | gggagtactg | taagataccg | tcctgtgact | cctccccagt | atccacggaa | 1080 |
| caattggctc | ccacagcacc | acctgagcta | accctgtgg | tccaggactg | ctaccatggt | 1140 |
| gatggacaga | gctaccgagg | cacatcctcc | accaccacca | caggaaagaa | gtgtcagtct | 1200 |
| tggtcatcta | tgacaccaca | ccggcaccag | aagacccag | aaaactaccc | aaatgctggc | 1260 |
| ctgacaatga | actactgcag | gaatccagat | gccgataaag | gccctggtg | ttttaccaca | 1320 |
| gaccccagcg | tcaggtggga | gtactgcaac | ctgaaaaaat | gctcaggaac | agaagcgagt | 1380 |
| gttgtagcac | ctccgcctgt | tgtcctgctt | ccagatgtag | agactccttc | cgaagaagac | 1440 |
| tgtatgtttg | ggaatgggaa | aggataccga | ggcaagaggg | cgaccactgt | tactgggacg | 1500 |
| ccatgccagg | actgggctgc | ccaggagccc | atagacaca | gcattttcac | tccagagaca | 1560 |
| aatccacggg | cgggtctgga | aaaaaattac | tgccgtaacc | ctgatggtga | tgtaggtggt | 1620 |
| ccctggtgct | acacgacaaa | tccaagaaaa | ctttacgact | actgtgatgt | ccctcagtgt | 1680 |
| gcggcccctt | catttgattg | tgggaagcct | caagtggagc | gaagaaatg | tcctggaagg | 1740 |
| gttgtagggg | gtgtgtggc | ccacccacat | tcctggccct | ggcaagtcag | tcttagaaca | 1800 |
| aggtttggaa | tgcacttctg | tggaggcacc | ttgatatccc | cagagtgggt | gttgactgct | 1860 |
| gcccactgct | tggagaagtc | cccaaggcct | tcatcctaca | aggtcatcct | gggtgcacac | 1920 |

```
caagaagtga atctcgaacc gcatgttcag gaaatagaag tgtctaggct gttcttggag    1980
cccacacgaa aagatattgc cttgctaaag ctaagcagtc ctgccgtcat cactgacaaa    2040
gtaatcccag cttgtctgcc atccccaaat tatgtggtcg ctgaccggac cgaatgtttc    2100
atcactggct ggggagaaac ccaaggtact tttggagctg ccttctcaa ggaagcccag     2160 ctccctgtga ttgagaataa agtgtgcaat cgctatgagt ttctgaatgg aagagtccaa    2220
tccaccgaac tctgtgctgg gcatttggcc ggaggcactg acagttgcca gggtgacagt    2280
ggaggtcctc tggtttgctt cgagaaggac aaatacattt acaaggagt cacttcttgg     2340 ggtcttggct gtgcacgccc caataagcct ggtgtctatg ttcgtgtttc aaggtttgtt    2400
acttggattg agggagtgat gagaaataat taa                                  2433
```

<210> SEQ ID NO 4
<211> LENGTH: 810
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Amino acid sequence coding for the natural plasminogen (from swiss prot)with the signal peptide

<400> SEQUENCE: 4

```
Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255
```

```
Cys Asp Ile Pro Arg Cys Thr Thr Pro Pro Ser Ser Gly Pro Thr
            260                 265                 270

Tyr Gln Cys Leu Lys Gly Thr Gly Glu Asn Tyr Arg Gly Asn Val Ala
        275                 280                 285

Val Thr Val Ser Gly His Thr Cys Gln His Trp Ser Ala Gln Thr Pro
290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
        355                 360                 365

Glu Leu Thr Pro Val Val Gln Asp Cys Tyr His Gly Asp Gly Gln Ser
370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
        435                 440                 445

Cys Asn Leu Lys Lys Cys Ser Gly Thr Glu Ala Ser Val Val Ala Pro
450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590

Pro Trp Gln Val Ser Leu Arg Thr Arg Phe Gly Met His Phe Cys Gly
        595                 600                 605

Gly Thr Leu Ile Ser Pro Glu Trp Val Leu Thr Ala Ala His Cys Leu
610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
            660                 665                 670
```

```
Ser Pro Ala Val Ile Thr Asp Lys Val Ile Pro Ala Cys Leu Pro Ser
            675                 680                 685

Pro Asn Tyr Val Ala Asp Arg Thr Glu Cys Phe Ile Thr Gly Trp
    690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 5
<211> LENGTH: 2145
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for LYS77-PLG(Lys-
      plasminogen)

<400> SEQUENCE: 5
aaagtgtatc tctcagagtg caagactggg aatggaaaga actacagagg gacgatgtcc     60
aaaacaaaaa atggcatcac ctgtcaaaaa tggagttcca cttctcccca cagacctaga   120
ttctcacctg ctacacaccc ctcagaggga ctggaggaga actactgcag gaatccagac   180
aacgatccgc aggggccctg tgctatact actgatccag aaaagagata tgactactgc   240
gacattcttg agtgtgaaga ggaatgtatg cattgcagtg agaaaactat gacggcaaa   300 atttccaaga ccatgtctgg actggaatgc caggcctggg actctcagag cccacacgct   360
catggataca ttccttccaa atttccaaac aagaacctga gaagaattac tgtcgtaac   420 cccgataggg agctgcggcc ttggtgtttc accaccgacc ccaacaagcg ctgggaactt   480
tgtgacatcc cccgctgcac aacacctcca ccatcttctg gtcccaccta ccagtgtctg   540
aagggaacag gtgaaaacta tcgcgggaat gtggctgtta ccgtgtccgg cacacctgt   600 cagcactgga gtgcacagac ccctcacaca cataacagga caccagaaaa cttcccctgc   660
aaaaatttgg atgaaaacta ctgccgcaat cctgacggaa aagggccccc atggtgccat   720
acaaccaaca gccaagtgcg gtgggagtac tgtaagatac cgtcctgtga ctcctcccca   780
gtatccacgg aacaattggc tcccacagca ccacctgagc taaccctgt ggtccaggac   840 tgctaccatg gtgatggaca gagctaccga ggcacatcct ccaccaccac cacaggaaag   900
aagtgtcagt cttggtcatc tatgacacca caccggcacc agaagacccc agaaaactac   960
ccaaatgctg gcctgacaat gaactactgc aggaatccag atgccgataa aggcccctgg   1020
tgttttacca cagaccccag cgtcaggtgg gagtactgca acctgaaaaa atgctcagga   1080
acagaagcga gtgttgtagc acctccgcct gttgtcctgc ttccagatgt agagactcct   1140
```

| | | |
|---|---|---|
| tccgaagaag actgtatgtt tgggaatggg aaaggatacc gaggcaagag ggcgaccact | 1200 | |
| gttactggga cgccatgcca ggactgggct gcccaggagc cccatagaca cagcattttc | 1260 | |
| actccagaga caaatccacg ggcgggtctg gaaaaaaatt actgccgtaa ccctgatggt | 1320 | |
| gatgtaggtg gtccctggtg ctacacgaca atccaagaa aactttacga ctactgtgat | 1380 | |
| gtccctcagt gtgcggcccc ttcatttgat tgtgggaagc tcaagtggaa gccgaagaaa | 1440 | |
| tgtcctggaa gggttgtagg ggggtgtgtg gcccacccac attcctggcc ctggcaagtc | 1500 | |
| agtcttagaa caaggtttgg aatgcacttc tgtggaggca ccttgatatc cccagagtgg | 1560 | |
| gtgttgactg ctgcccactg cttggagaag tccccaaggc cttcatccta caaggtcatc | 1620 | |
| ctgggtgcac accaagaagt gaatctcgaa ccgcatgttc aggaaataga agtgtctagg | 1680 | |
| ctgttcttgg agcccacacg aaaagatatt gccttgctaa agctaagcag tcctgccgtc | 1740 | |
| atcactgaca aagtaatccc agcttgtctg ccatccccaa attatgtggt cgctgaccgg | 1800 | |
| accgaatgtt tcatcactgg ctggggagaa acccaaggta cttttggagc tggccttctc | 1860 | |
| aaggaagccc agctccctgt gattgagaat aaagtgtgca atcgctatga gtttctgaat | 1920 | |
| ggaagagtcc aatccaccga actctgtgct gggcatttgg ccggaggcac tgacagttgc | 1980 | |
| cagggtgaca gtggaggtcc tctggtttgc ttcgagaagg acaaatacat tttacaagga | 2040 | |
| gtcacttctt ggggtcttgg ctgtgcacgc cccaataagc ctggtgtcta tgttcgtgtt | 2100 | |
| tcaaggtttg ttacttggat tgagggagtg atgagaaata attaa | 2145 | |

```
<210> SEQ ID NO 6
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of LYS77-PLG(Lys-
      plasminogen)

<400> SEQUENCE: 6
```

Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Pro Ser Ser Gly Pro Thr

```
            165                 170                 175
Tyr Gln Cys Leu Lys Gly Thr Gly Glu Asn Tyr Arg Gly Asn Val Ala
                180                 185                 190

Val Thr Val Ser Gly His Thr Cys Gln His Trp Ser Ala Gln Thr Pro
            195                 200                 205

His Thr His Asn Arg Thr Pro Glu Asn Phe Pro Cys Lys Asn Leu Asp
        210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro Pro Val Val Leu Leu Pro Asp Val Glu Thr Pro Ser Glu Glu Asp
    370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
                405                 410                 415

His Ser Ile Phe Thr Pro Glu Thr Asn Pro Arg Ala Gly Leu Glu Lys
            420                 425                 430

Asn Tyr Cys Arg Asn Pro Asp Gly Asp Val Gly Gly Pro Trp Cys Tyr
        435                 440                 445

Thr Thr Asn Pro Arg Lys Leu Tyr Asp Tyr Cys Asp Val Pro Gln Cys
    450                 455                 460

Ala Ala Pro Ser Phe Asp Cys Gly Lys Pro Gln Val Glu Pro Lys Lys
465                 470                 475                 480

Cys Pro Gly Arg Val Val Gly Gly Cys Val Ala His Pro His Ser Trp
                485                 490                 495

Pro Trp Gln Val Ser Leu Arg Thr Arg Phe Gly Met His Phe Cys Gly
            500                 505                 510

Gly Thr Leu Ile Ser Pro Glu Trp Val Leu Thr Ala Ala His Cys Leu
        515                 520                 525

Glu Lys Ser Pro Arg Pro Ser Ser Tyr Lys Val Ile Leu Gly Ala His
    530                 535                 540

Gln Glu Val Asn Leu Glu Pro His Val Gln Glu Ile Glu Val Ser Arg
545                 550                 555                 560

Leu Phe Leu Glu Pro Thr Arg Lys Asp Ile Ala Leu Leu Lys Leu Ser
                565                 570                 575

Ser Pro Ala Val Ile Thr Asp Lys Val Ile Pro Ala Cys Leu Pro Ser
            580                 585                 590
```

```
Pro Asn Tyr Val Val Ala Asp Arg Thr Glu Cys Phe Ile Thr Gly Trp
        595                 600                 605

Gly Glu Thr Gln Gly Thr Phe Gly Ala Gly Leu Leu Lys Glu Ala Gln
610                 615                 620

Leu Pro Val Ile Glu Asn Lys Val Cys Asn Arg Tyr Glu Phe Leu Asn
625                 630                 635                 640

Gly Arg Val Gln Ser Thr Glu Leu Cys Ala Gly His Leu Ala Gly Gly
            645                 650                 655

Thr Asp Ser Cys Gln Gly Asp Ser Gly Gly Pro Leu Val Cys Phe Glu
            660                 665                 670

Lys Asp Lys Tyr Ile Leu Gln Gly Val Thr Ser Trp Gly Leu Gly Cys
        675                 680                 685

Ala Arg Pro Asn Lys Pro Gly Val Tyr Val Arg Val Ser Arg Phe Val
    690                 695                 700

Thr Trp Ile Glu Gly Val Met Arg Asn Asn
705                 710
```

<210> SEQ ID NO 7
<211> LENGTH: 1245
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for delta-plg(delta-
      plasminogen)

<400> SEQUENCE: 7

```
gagcctctgg atgactatgt gaatacccag ggggcttcac tgttcagtgt cactaagaag        60
cagctgggag caggaagtat agaagaatgt gcagcaaaat gtgaggagga cgaagaattc       120
acctgcaggg cattccaata tcacagtaaa gagcaacaat gtgtgataat ggctgaaaac       180
aggaagtcct ccataatcat taggatgaga gatgtagttt tatttgaaaa gaaagtgtat       240
ctctcagagt gcaagactgg aatggaaag aactacagag ggacgatgtc caaaacaaaa        300
aatggcatca cctgtcaaaa atggagttcc acttctcccc acagacctag attctcacct       360
gctacacacc cctcagaggg actggaggag aactactgca ggaatccaga caacgatccg       420
caggggcccc ggtgctatac tactgatcca gaaagagatg atgactactg cgacattctt       480
gagtgtgaag aggcggcccc ttcatttgat tgtgggaagc tcaagtgga gccgaagaaa        540
tgtcctggaa gggttgtagg ggggtgtgtg gcccacccac attcctggcc ctggcaagtc       600
agtcttagaa caaggtttgg aatgcacttc tgtggaggca ccttgatatc cccagagtgg       660
gtgttgactg ctgcccactg cttggagaag tccccaaggc cttcatccta caaggtcatc       720
ctgggtgcac accaagaagt gaatctcgaa ccgcatgttc aggaaataga agtgtctagg       780
ctgttcttgg agcccacacg aaaagatatt gccttgctaa agctaagcag tcctgccgtc       840
atcactgaca aagtaatccc agcttgtctg ccatccccaa attatgtggt cgctgaccgg       900
accgaatgtt tcatcactgg ctggggagaa acccaaggta cttttggagc tggccttctc       960
aaggaagccc agctccctgt gattgagaat aaagtgtgca atcgctatga gtttctgaat      1020
ggaagagtcc aatccaccga actctgtgct gggcatttgg ccggaggcac tgacagttgc      1080
cagggtgaca gtgaggtcc tctggtttgc ttcgagaagg acaaatacat tttacaagga      1140
gtcacttctt ggggtcttgg ctgtgcacgc cccaataagc ctggtgtcta tgttcgtgtt      1200
```
tcaaggtttg ttacttggat tgagggagtg atgagaaata attaa            1245

<210> SEQ ID NO 8
<211> LENGTH: 414
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of delta-plg(delta-
      plasminogen)

<400> SEQUENCE: 8

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Ala Ala Pro Ser Phe Asp Cys Gly Lys Pro Gln Val
                165                 170                 175

Glu Pro Lys Lys Cys Pro Gly Arg Val Val Gly Gly Cys Val Ala His
            180                 185                 190

Pro His Ser Trp Pro Trp Gln Val Ser Leu Arg Thr Arg Phe Gly Met
        195                 200                 205

His Phe Cys Gly Gly Thr Leu Ile Ser Pro Glu Trp Val Leu Thr Ala
    210                 215                 220

Ala His Cys Leu Glu Lys Ser Pro Arg Pro Ser Ser Tyr Lys Val Ile
225                 230                 235                 240

Leu Gly Ala His Gln Glu Val Asn Leu Glu Pro His Val Gln Glu Ile
                245                 250                 255

Glu Val Ser Arg Leu Phe Leu Glu Pro Thr Arg Lys Asp Ile Ala Leu
            260                 265                 270

Leu Lys Leu Ser Ser Pro Ala Val Ile Thr Asp Lys Val Ile Pro Ala
        275                 280                 285

Cys Leu Pro Ser Pro Asn Tyr Val Val Ala Asp Arg Thr Glu Cys Phe
    290                 295                 300

Ile Thr Gly Trp Gly Glu Thr Gln Gly Thr Phe Gly Ala Gly Leu Leu
305                 310                 315                 320

Lys Glu Ala Gln Leu Pro Val Ile Glu Asn Lys Val Cys Asn Arg Tyr
                325                 330                 335

Glu Phe Leu Asn Gly Arg Val Gln Ser Thr Glu Leu Cys Ala Gly His
                340                 345                 350

Leu Ala Gly Gly Thr Asp Ser Cys Gln Gly Asp Ser Gly Gly Pro Leu
            355                 360                 365

Val Cys Phe Glu Lys Asp Lys Tyr Ile Leu Gln Gly Val Thr Ser Trp
370                 375                 380

Gly Leu Gly Cys Ala Arg Pro Asn Lys Pro Gly Val Tyr Val Arg Val
385                 390                 395                 400

Ser Arg Phe Val Thr Trp Ile Glu Gly Val Met Arg Asn Asn
                405                 410

<210> SEQ ID NO 9
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for Mini-plg(mini-
      plasminogen)

<400> SEQUENCE: 9
gtcaggtggg agtactgcaa cctgaaaaaa tgctcaggaa cagaagcgag tgttgtagca        60
cctccgcctg ttgtcctgct tccagatgta gagactcctt ccgaagaaga ctgtatgttt       120
gggaatggga aggataccg aggcaagagg gcgaccactg ttactgggac gccatgccag        180
gactgggctg cccaggagcc ccatagacac agcattttca ctccagagac aaatccacgg       240
gcgggtctgg aaaaaaatta ctgccgtaac cctgatggtg atgtaggtgg tccctggtgc       300
tacacgacaa atccaagaaa actttacgac tactgtgatg tccctcagtg tgcggcccct       360
tcatttgatt gtgggaagcc tcaagtggag ccgaagaaat gtcctggaag ggttgtaggg       420
gggtgtgtgg cccacccaca ttcctggccc tggcaagtca gtcttagaac aaggtttgga       480
atgcacttct gtggaggcac cttgatatcc ccagagtggg tgttgactgc tgcccactgc       540
ttggagaagt ccccaaggcc ttcatcctac aaggtcatcc tgggtgcaca ccaagaagtg       600
aatctcgaac cgcatgttca ggaaatagaa gtgtctaggc tgttcttgga gcccacacga       660
aaagatattg ccttgctaaa gctaagcagt cctgccgtca tcactgacaa agtaatccca       720
gcttgtctgc catccccaaa ttatgtggtc gctgaccgga ccgaatgttt catcactggc       780
tggggagaaa cccaaggtac ttttggagct ggccttctca aggaagccca gctccctgtg       840
attgagaata aagtgtgcaa tcgctatgag tttctgaatg gaagagtcca atccaccgaa       900
ctctgtgctg gcatttggc cggaggcact gacagttgcc agggtgacag tggaggtcct       960
ctggtttgct tcgagaagga caaatacatt ttacaaggag tcacttcttg gggtcttggc      1020
tgtgcacgcc ccaataagcc tggtgtctat gttcgtgttt caaggtttgt tacttggatt      1080
gagggagtga tgagaaataa ttaa                                             1104

<210> SEQ ID NO 10
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of Mini-plg(mini-
      plasminogen)

<400> SEQUENCE: 10

```
Val Arg Trp Glu Tyr Cys Asn Leu Lys Lys Cys Ser Gly Thr Glu Ala
1               5                   10                  15
Ser Val Val Ala Pro Pro Val Val Leu Leu Pro Asp Val Glu Thr
            20                  25                  30
Pro Ser Glu Glu Asp Cys Met Phe Gly Asn Gly Lys Gly Tyr Arg Gly
        35                  40                  45
Lys Arg Ala Thr Thr Val Thr Gly Thr Pro Cys Gln Asp Trp Ala Ala
    50                  55                  60
Gln Glu Pro His Arg His Ser Ile Phe Thr Pro Glu Thr Asn Pro Arg
65                  70                  75                  80
Ala Gly Leu Glu Lys Asn Tyr Cys Arg Asn Pro Asp Gly Asp Val Gly
                85                  90                  95
Gly Pro Trp Cys Tyr Thr Thr Asn Pro Arg Lys Leu Tyr Asp Tyr Cys
            100                 105                 110
Asp Val Pro Gln Cys Ala Ala Pro Ser Phe Asp Cys Gly Lys Pro Gln
        115                 120                 125
Val Glu Pro Lys Lys Cys Pro Gly Arg Val Val Gly Gly Cys Val Ala
    130                 135                 140
His Pro His Ser Trp Pro Trp Gln Val Ser Leu Arg Thr Arg Phe Gly
145                 150                 155                 160
Met His Phe Cys Gly Gly Thr Leu Ile Ser Pro Glu Trp Val Leu Thr
                165                 170                 175
Ala Ala His Cys Leu Glu Lys Ser Pro Arg Pro Ser Ser Tyr Lys Val
            180                 185                 190
Ile Leu Gly Ala His Gln Glu Val Asn Leu Glu Pro His Val Gln Glu
        195                 200                 205
Ile Glu Val Ser Arg Leu Phe Leu Glu Pro Thr Arg Lys Asp Ile Ala
    210                 215                 220
Leu Leu Lys Leu Ser Ser Pro Ala Val Ile Thr Asp Lys Val Ile Pro
225                 230                 235                 240
Ala Cys Leu Pro Ser Pro Asn Tyr Val Val Ala Asp Arg Thr Glu Cys
                245                 250                 255
Phe Ile Thr Gly Trp Gly Glu Thr Gln Gly Thr Phe Gly Ala Gly Leu
            260                 265                 270
Leu Lys Glu Ala Gln Leu Pro Val Ile Glu Asn Lys Val Cys Asn Arg
        275                 280                 285
Tyr Glu Phe Leu Asn Gly Arg Val Gln Ser Thr Glu Leu Cys Ala Gly
    290                 295                 300
His Leu Ala Gly Gly Thr Asp Ser Cys Gln Gly Asp Ser Gly Gly Pro
305                 310                 315                 320
Leu Val Cys Phe Glu Lys Asp Lys Tyr Ile Leu Gln Gly Val Thr Ser
                325                 330                 335
Trp Gly Leu Gly Cys Ala Arg Pro Asn Lys Pro Gly Val Tyr Val Arg
            340                 345                 350
Val Ser Arg Phe Val Thr Trp Ile Glu Gly Val Met Arg Asn Asn
        355                 360                 365

<210> SEQ ID NO 11
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<223> OTHER INFORMATION: Nucleotide sequence coding for Micro-plg(micro-
      plasminogen)

<400> SEQUENCE: 11
gccccttcat tgattgtgg gaagcctcaa gtggagccga agaaatgtcc tggaagggtt      60
gtaggggggt gtgtggccca cccacattcc tggccctggc aagtcagtct tagaacaagg     120
tttggaatgc acttctgtgg aggcaccttg atatccccag agtgggtgtt gactgctgcc    180
cactgcttgg agaagtcccc aaggccttca tcctacaagg tcatcctggg tgcacaccaa    240
gaagtgaatc tcgaaccgca tgttcaggaa atagaagtgt ctaggctgtt cttggagccc    300
acacgaaaag atattgcctt gctaaagcta agcagtcctg ccgtcatcac tgacaaagta    360
atcccagctt gtctgccatc cccaaattat gtggtcgctg accggaccga atgtttcatc    420
actggctggg gagaaaccca aggtactttt ggagctggcc ttctcaagga agcccagctc    480
cctgtgattg agaataaagt gtgcaatcgc tatgagtttc tgaatggaag agtccaatcc    540
accgaactct gtgctgggca tttggccgga ggcactgaca gttgccaggg tgacagtgga    600
ggtcctctgg tttgcttcga gaaggacaaa tacattttac aaggagtcac ttcttggggt    660
cttggctgtg cacgccccaa taagcctggt gtctatgttc gtgtttcaag gtttgttact    720
tggattgagg gagtgatgag aaataattaa                                     750

<210> SEQ ID NO 12
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence coding for Micro-plg(micro-
      plasminogen)

<400> SEQUENCE: 12

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175
```

Arg Val Gln Ser Thr Glu Leu Cys Ala Gly His Leu Ala Gly Gly Thr
            180                 185                 190

Asp Ser Cys Gln Gly Asp Ser Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 13
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for the serine
      protease domain

<400> SEQUENCE: 13
gttgtagggg ggtgtgtggc ccacccacat tcctggccct ggcaagtcag tcttagaaca     60
aggtttggaa tgcacttctg tggaggcacc ttgatatccc cagagtgggt gttgactgct    120
gcccactgct tggagaagtc cccaaggcct tcatcctaca aggtcatcct gggtgcacac    180
caagaagtga atctcgaacc gcatgttcag gaaatagaag tgtctaggct gttcttggag    240
cccacacgaa aagatattgc cttgctaaag ctaagcagtc ctgccgtcat cactgacaaa    300
gtaatcccag cttgtctgcc atccccaaat tatgtggtcg ctgaccggac cgaatgtttc    360
atcactggct ggggagaaac ccaaggtact tttggagctg gccttctcaa ggaagcccag    420
ctccctgtga ttgagaataa agtgtgcaat cgctatgagt ttctgaatgg aagagtccaa    480
tccaccgaac tctgtgctgg gcatttggcc ggaggcactg acagttgcca gggtgacagt    540
ggaggtcctc tggtttgctt cgagaaggac aaatacattt tacaaggagt cacttcttgg    600
ggtcttggct gtgcacgccc caataagcct ggtgtctatg ttcgtgtttc aaggtttgtt    660
acttggattg agggagtgat gaga                                           684

<210> SEQ ID NO 14
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence coding for the serine
      protease domain

<400> SEQUENCE: 14

Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
            20                  25                  30

Ser Pro Glu Trp Val Leu Thr Ala Ala His Cys Leu Glu Lys Ser Pro
        35                  40                  45

Arg Pro Ser Ser Tyr Lys Val Ile Leu Gly Ala His Gln Glu Val Asn
    50                  55                  60

-continued

```
Leu Glu Pro His Val Gln Glu Ile Glu Val Ser Arg Leu Phe Leu Glu
 65              70                  75                  80

Pro Thr Arg Lys Asp Ile Ala Leu Leu Lys Leu Ser Ser Pro Ala Val
             85                  90                  95

Ile Thr Asp Lys Val Ile Pro Ala Cys Leu Pro Ser Pro Asn Tyr Val
            100                 105                 110

Val Ala Asp Arg Thr Glu Cys Phe Ile Thr Gly Trp Gly Glu Thr Gln
        115                 120                 125

Gly Thr Phe Gly Ala Gly Leu Leu Lys Glu Ala Gln Leu Pro Val Ile
        130                 135                 140

Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                165                 170                 175

Gln Gly Asp Ser Gly Gly Pro Leu Val Cys Phe Glu Lys Asp Lys Tyr
            180                 185                 190

Ile Leu Gln Gly Val Thr Ser Trp Gly Leu Gly Cys Ala Arg Pro Asn
        195                 200                 205

Lys Pro Gly Val Tyr Val Arg Val Ser Arg Phe Val Thr Trp Ile Glu
    210                 215                 220

Gly Val Met Arg
225
```